(12) United States Patent
Karpen et al.

(10) Patent No.: US 8,514,278 B2
(45) Date of Patent: Aug. 20, 2013

(54) INSPECTION APPARATUS HAVING ILLUMINATION ASSEMBLY

(75) Inventors: Thomas W. Karpen, Skaneateles, NY (US); Bradford Morse, Syracuse, NY (US); James Jonathon Delmonico, Baldwinsville, NY (US)

(73) Assignee: GE Inspection Technologies LP, Schenectady, NY (US)

( * ) Notice: Subject to any disclaimer, the term of this patent is extended or adjusted under 35 U.S.C. 154(b) by 1999 days.

(21) Appl. No.: 11/648,189

(22) Filed: Dec. 29, 2006

(65) Prior Publication Data
US 2008/0158348 A1 Jul. 3, 2008

(51) Int. Cl.
*H04N 5/253* (2006.01)

(52) U.S. Cl.
USPC .............. 348/80; 348/84; 348/69; 600/179; 600/109; 600/180; 385/117

(58) Field of Classification Search
USPC ............... 348/80, 84, 69, 117; 600/156, 179, 600/180
See application file for complete search history.

(56) References Cited

U.S. PATENT DOCUMENTS

| | | |
|---|---|---|
| 2,844,987 A | 7/1958 | Parker |
| 2,932,294 A | 4/1960 | Fourestier et al. |
| 3,299,274 A | 1/1967 | Hoelter |
| 3,603,722 A | 9/1971 | Graham |
| 3,641,256 A | 2/1972 | Davis, Jr. |
| 3,944,327 A | 3/1976 | Larsen |
| 4,266,534 A | 5/1981 | Ogawa |
| 4,272,156 A | 6/1981 | Ishibashi et al. |
| 4,410,914 A | 10/1983 | Siau |
| 4,415,240 A | 11/1983 | Nishioka et al. |
| 4,421,383 A | 12/1983 | Carlsen |
| 4,476,494 A | 10/1984 | Tugaye et al. |
| 4,532,918 A | 8/1985 | Wheeler |
| 4,546,379 A | 10/1985 | Sarofeen et al. |
| 4,580,522 A | 4/1986 | Fujioka et al. |
| 4,666,246 A | 5/1987 | Nishioka et al. |
| 4,681,093 A | 7/1987 | Ono et al. |
| 4,700,693 A | 10/1987 | Lia et al. |
| 4,727,859 A | 3/1988 | Lia |
| 4,733,937 A | 3/1988 | Lia et al. |
| 4,735,501 A | 4/1988 | Ginsburgh et al. |
| 4,787,369 A | 11/1988 | Allred, III et al. |
| 4,790,294 A | 12/1988 | Allred, III et al. |
| 4,794,912 A | 1/1989 | Lia |
| 4,796,607 A | 1/1989 | Allred, III et al. |

(Continued)

FOREIGN PATENT DOCUMENTS

| EP | 1488731 A | 12/2004 |
|---|---|---|
| EP | 1859727 A | 11/2007 |

(Continued)

OTHER PUBLICATIONS

US 6,692,429, 02/2004, Imaizumi et al. (withdrawn)

*Primary Examiner* — Tammy Nguyen

(74) *Attorney, Agent, or Firm* — Hiscock & Barclay LLP

(57) ABSTRACT

An inspection apparatus can comprise at least one light source for illuminating a target. The at least one light source can be disposed and/or controlled in such manner as to reduce a heat generation by the at least one light source and in such manner as to reduce a power consumption of the at least one light source.

23 Claims, 9 Drawing Sheets

(56) References Cited

U.S. PATENT DOCUMENTS

| | | | |
|---|---|---|---|
| 4,802,460 | A | 2/1989 | Ohkuwa et al. |
| 4,823,244 | A | 4/1989 | Alaybayoglu et al. |
| 4,853,774 | A | 8/1989 | Danna et al. |
| 4,862,253 | A | 8/1989 | English et al. |
| 4,862,258 | A | 8/1989 | Kidawara et al. |
| 4,871,229 | A | 10/1989 | Tashiro |
| 4,879,592 | A | 11/1989 | Ernest |
| 4,884,133 | A | 11/1989 | Kanno et al. |
| 4,885,635 | A | 12/1989 | Kimura et al. |
| 4,887,154 | A | 12/1989 | Wawro et al. |
| 4,901,143 | A | 2/1990 | Uehara et al. |
| 4,909,600 | A | 3/1990 | Ciarlei et al. |
| 4,913,369 | A | 4/1990 | Lia et al. |
| 4,924,856 | A * | 5/1990 | Noguchi ................ 600/180 |
| 4,928,172 | A * | 5/1990 | Uehara et al. ............ 348/69 |
| 4,941,454 | A | 7/1990 | Wood et al. |
| 4,941,456 | A | 7/1990 | Wood et al. |
| 4,957,346 | A * | 9/1990 | Wood et al. ............. 385/117 |
| 4,962,751 | A | 10/1990 | Krauter |
| 4,980,763 | A | 12/1990 | Lia |
| 4,989,581 | A | 2/1991 | Tamburrino et al. |
| 4,998,166 | A | 3/1991 | Salvati |
| 4,998,182 | A | 3/1991 | Krauter et al. |
| 5,014,515 | A | 5/1991 | Krauter |
| 5,014,600 | A | 5/1991 | Krauter et al. |
| 5,018,436 | A | 5/1991 | Evangelista et al. |
| 5,018,506 | A | 5/1991 | Danna et al. |
| 5,019,121 | A | 5/1991 | Krauter |
| 5,032,913 | A | 7/1991 | Hattori et al. |
| 5,047,848 | A | 9/1991 | Krauter |
| 5,052,803 | A | 10/1991 | Krauter |
| 5,061,995 | A | 10/1991 | Lia et al. |
| 5,066,122 | A | 11/1991 | Krauter |
| 5,070,401 | A | 12/1991 | Salvati et al. |
| 5,096,292 | A * | 3/1992 | Sakamoto et al. ......... 356/241.4 |
| 5,114,636 | A | 5/1992 | Evangelista et al. |
| 5,140,975 | A | 8/1992 | Krauter |
| 5,164,824 | A | 11/1992 | Ieoka et al. |
| 5,191,879 | A | 3/1993 | Krauter |
| 5,202,758 | A | 4/1993 | Tamburrino |
| 5,203,319 | A | 4/1993 | Danna et al. |
| 5,270,810 | A | 12/1993 | Nishimura et al. |
| 5,275,152 | A | 1/1994 | Krauter et al. |
| 5,278,642 | A | 1/1994 | Danna et al. |
| 5,314,070 | A | 5/1994 | Ciarlei |
| 5,323,899 | A | 6/1994 | Strom et al. |
| 5,331,949 | A * | 7/1994 | Funakoshi et al. ......... 600/109 |
| 5,345,339 | A | 9/1994 | Knieriem et al. |
| 5,347,989 | A | 9/1994 | Monroe et al. |
| 5,365,331 | A | 11/1994 | Tamburrino et al. |
| 5,371,384 | A | 12/1994 | Wada |
| 5,373,317 | A | 12/1994 | Salvati et al. |
| 5,387,928 | A | 2/1995 | Nishimura et al. |
| 5,402,165 | A | 3/1995 | Linville et al. |
| D358,471 | S | 5/1995 | Cope et al. |
| 5,420,644 | A | 5/1995 | Watanabe et al. |
| 5,435,296 | A | 7/1995 | Vivenzio et al. |
| 5,469,210 | A | 11/1995 | Noguchi et al. |
| 5,515,449 | A | 5/1996 | Tsuruoka et al. |
| 5,568,190 | A | 10/1996 | Noguchi et al. |
| 5,592,328 | A | 1/1997 | Greenberg |
| 5,617,136 | A | 4/1997 | Iso et al. |
| 5,631,695 | A | 5/1997 | Nakamura et al. |
| 5,633,675 | A | 5/1997 | Danna et al. |
| 5,701,155 | A | 12/1997 | Wood et al. |
| 5,734,418 | A | 3/1998 | Danna |
| 5,754,313 | A | 5/1998 | Pelchy et al. |
| 5,796,427 | A | 8/1998 | Suzuki et al. |
| 5,857,963 | A | 1/1999 | Pelchy et al. |
| 5,956,416 | A | 9/1999 | Tsuruoka et al. |
| 5,990,471 | A | 11/1999 | Watanabe |
| 6,040,946 | A | 3/2000 | Hebert |
| 6,083,152 | A | 7/2000 | Strong |
| 6,097,848 | A | 8/2000 | Salvati |
| 6,120,435 | A | 9/2000 | Eino et al. |
| 6,166,496 | A | 12/2000 | Lys et al. |
| 6,211,626 | B1 | 4/2001 | Lys et al. |
| 6,260,994 | B1 | 7/2001 | Matsumoto et al. |
| 6,290,382 | B1 | 9/2001 | Bourn et al. |
| 6,331,156 | B1 | 12/2001 | Haefele et al. |
| 6,438,302 | B1 | 8/2002 | Utsui et al. |
| 6,468,201 | B1 | 10/2002 | Burdick |
| 6,483,535 | B1 | 11/2002 | Tamburrino et al. |
| 6,494,739 | B1 | 12/2002 | Vivenzio et al. |
| 6,527,708 | B1 | 3/2003 | Nakamura et al. |
| 6,538,732 | B1 | 3/2003 | Drost et al. |
| 6,545,260 | B1 * | 4/2003 | Katashiro et al. ........ 250/227.26 |
| 6,590,470 | B1 | 7/2003 | Burdick |
| 6,692,431 | B2 | 2/2004 | Kazakevich |
| 6,730,019 | B2 | 5/2004 | Irion |
| 6,734,893 | B1 | 5/2004 | Hess et al. |
| 6,796,939 | B1 * | 9/2004 | Hirata et al. ............. 600/179 |
| 6,814,699 | B2 | 11/2004 | Ross et al. |
| 6,830,545 | B2 | 12/2004 | Bendall |
| 6,831,679 | B1 * | 12/2004 | Olsson et al. ............ 348/84 |
| 6,918,693 | B2 | 7/2005 | Ota et al. |
| 6,921,920 | B2 | 7/2005 | Kazakevich |
| 6,953,432 | B2 | 10/2005 | Schiefer |
| 7,037,259 | B2 | 5/2006 | Hakamata et al. |
| 7,041,054 | B2 | 5/2006 | Klootz |
| 7,048,686 | B2 | 5/2006 | Kameya et al. |
| 7,063,663 | B2 | 6/2006 | Kazakevich |
| 7,077,804 | B2 | 7/2006 | Ota |
| 7,087,014 | B2 | 8/2006 | Sasaki |
| 7,134,993 | B2 | 11/2006 | Lia et al. |
| 7,335,159 | B2 * | 2/2008 | Banik et al. ............. 600/156 |
| 2002/0120181 | A1 | 8/2002 | Irior |
| 2003/0202090 | A1 | 10/2003 | Ota |
| 2004/0162492 | A1 | 8/2004 | Kobatashi |
| 2004/0183900 | A1 | 9/2004 | Karpen et al. |
| 2004/0215413 | A1 | 10/2004 | Weldum et al. |
| 2005/0050707 | A1 | 3/2005 | Scott et al. |
| 2005/0075538 | A1 | 4/2005 | Banik et al. |
| 2005/0129108 | A1 | 6/2005 | Bendall et al. |
| 2005/0154262 | A1 | 7/2005 | Banik et al. |
| 2005/0162643 | A1 | 7/2005 | Karpen |
| 2005/0276553 | A1 | 12/2005 | Kazakevich |
| 2005/0281520 | A1 | 12/2005 | Kehoskie et al. |
| 2006/0050983 | A1 | 3/2006 | Bendall et al. |
| 2006/0069314 | A1 | 3/2006 | Farr |
| 2006/0072903 | A1 | 4/2006 | Weldum et al. |
| 2006/0116553 | A1 | 6/2006 | Dunki-Jacobs et al. |
| 2006/0171693 | A1 | 8/2006 | Todd et al. |

FOREIGN PATENT DOCUMENTS

| | | |
|---|---|---|
| JP | 60232525 A | 11/1985 |
| JP | 61004015 A | 1/1986 |
| JP | 63309912 A | 12/1988 |
| JP | 5146403 A | 6/1993 |
| JP | 2001292956 A | 10/2001 |
| JP | 2002112959 A | 4/2002 |
| JP | 2003019112 A | 1/2003 |
| JP | 2003255236 A | 9/2003 |
| JP | 2004029235 A | 1/2004 |
| JP | 2005087551 A | 4/2005 |
| JP | 2006034723 A | 2/2006 |
| JP | 2006087764 A | 4/2006 |
| WO | WO00/33727 A | 6/2000 |
| WO | WO-03071333 A1 | 8/2003 |
| WO | WO2004/082472 A | 9/2004 |
| WO | WO-2004103146 A2 | 12/2004 |
| WO | WO2006/099738 A | 9/2006 |
| WO | WO2006/106853 A | 10/2006 |

* cited by examiner

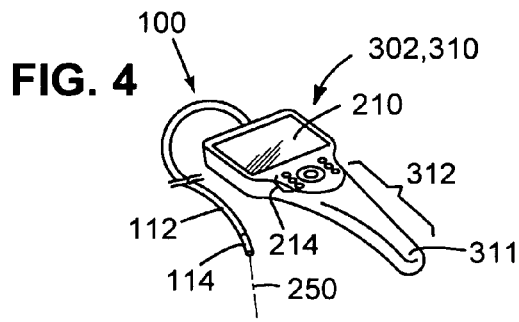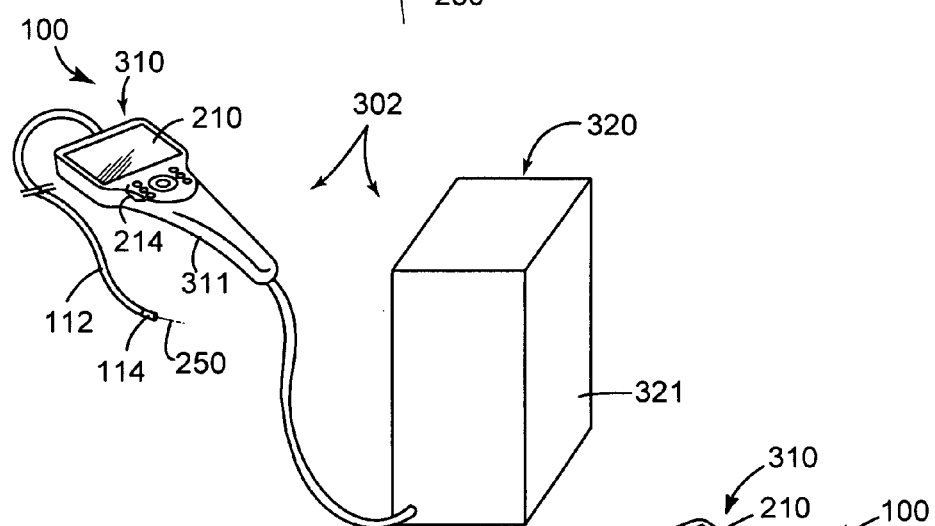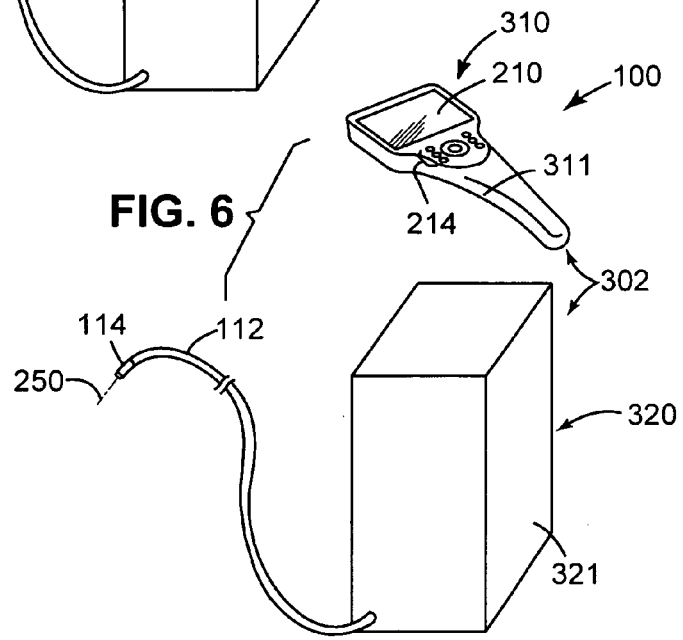

US 8,514,278 B2

INSPECTION APPARATUS HAVING ILLUMINATION ASSEMBLY

FIELD OF THE INVENTION

The invention relates to inspection apparatuses and more particularly to visual inspection apparatuses.

BACKGROUND OF THE PRIOR ART

Various proposals have been made for the inspection apparatus illumination assemblies. In U.S. Pat. No. 4,957,346, assigned to the assignee of the present invention, there is described an inspection apparatus illumination assembly wherein a light source provided by a halogen lamp is turned on at video frequencies and the duration of actuation is controlled in relation to the illumination picked up by an image sensor. In U.S. Pat. No. 4,998,166, also assigned to the assignee of the present invention, an inspection apparatus is provided with an auxiliary light box. An inspection tube of the inspection apparatus can be interfaced to the auxiliary light box. Sequential primary color illumination is generated in the auxiliary light box and supplied to a fiber optic bundle in the insertion tube.

BRIEF DESCRIPTION OF THE DRAWINGS

FIGS. 4-6 are diagrams illustrating various alternative packaging schemes for an inspection apparatus.

DETAILED DESCRIPTION OF THE INVENTION

Figure 1:
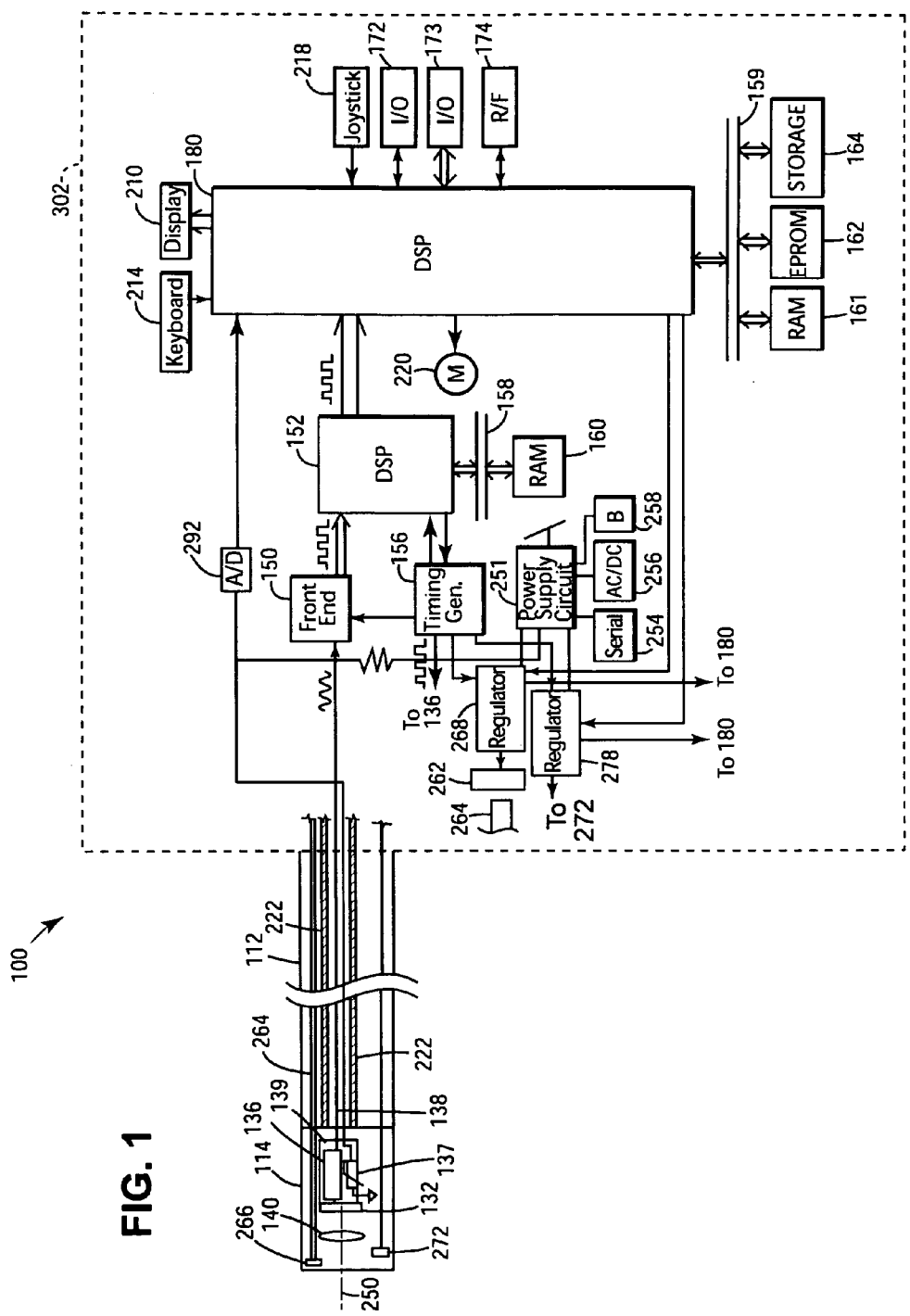
FIG. 1 is a block diagram illustrating an inspection apparatus in one embodiment.

There is described an inspection apparatus having an illumination assembly wherein the illumination assembly comprises at least one light source. In one embodiment the illumination assembly can be arranged and controlled for purposes of reducing an amount of heat generated by the illumination assembly, for purposes of reducing power consumption of the illumination assembly, and for purposes of reducing noise in a video signal resulting from excess heat.

A packaging scheme for an inspection apparatus in one embodiment can be adopted wherein a first light source bank is provided at a distal end of a probe and a second light source bank is provided at a proximal end of the probe. Each light source bank can have one or more light sources and in one embodiment the one or more light sources can be provided by LEDs. The first light source bank and the second light source bank can be controlled in a coordinated manner so that in a first mode of operation, only the first light source bank is energized, in a second mode of operation, the first and second light source bank are energized and in a third mode of operation, both of the first bank and the second bank are energized.

In one example of an inspection apparatus having first and second spaced apart light source banks, the first light source bank can be normally on and the second light source bank can be energized on an as-needed basis on the condition that a brightness of a captured frame of image data has fallen below a threshold brightness.

In one embodiment, a light source bank can be controlled in such manner as to reduce heat generated by the light source bank and to reduce power consumption of a light source bank. A light source bank driver signal can be provided in a coordinated manner with an exposure control pulse, specifically, a light source bank driver signal can be provided by a square wave pulse having duty cycle illumination off time periods intermediate of illumination on time periods. For reduction of heat generation and power consumption without reduction of image brightness, a light source bank driver signal can be provided in a coordinated manner with an exposure control signal so that a light source bank is selectively energized only during exposure periods of an image sensor.

In one embodiment, a light source bank can be disposed proximate an image sensor or another sensitive electrical component having a performance and/or expected life that is negatively impacted by heat. In one embodiment, an inspection apparatus can be configured to sense a temperature of the sensitive electrical component and to regulate at least one of a peak power level and a duty cycle of the light source bank driver signal so as to reduce heat generated by the light source bank where a temperature of the sensitive electrical component exceeds a threshold.

A technical effect of the hardware and software described herein in certain embodiments is reduced heat in an inspection apparatus. By reducing heat absorption by electrical components of an inspection apparatus, performance and life expectancy of the electrical component can be expected to improve. A technical effect of the hardware and software described herein in certain embodiments is reduced power consumption. A further technical effect of the hardware and software herein is reduced visual noise.

A block diagram of an exemplary apparatus capable of supporting the above described processing is shown and described in connection with FIG. 1. Inspection apparatus 100 can include an elongated inspection tube 112 and a head assembly 114 disposed at a distal end of the elongated inspection module. Inspection apparatus 100 can also include a base assembly 302 disposed at a proximal end of elongated inspection tube 112.

Regarding head assembly 114, head assembly 114 can include solid state image sensor 132 and imaging optics 140 comprising one or more lenses. Imaging optics 140 can focus an image onto an active surface of solid state image sensor 132. Solid state image sensor 132 can be, e.g., a CCD or CMOS image sensor. Solid state image sensor 132 can include a plurality of pixels formed in a plurality of rows and columns. Where solid state image sensor 132 includes a plurality of pixels formed in a plurality of rows and columns, solid state image sensor 132 can be regarded as a two dimensional image sensor. Solid state image sensor 132 can be provided on an integrated circuit. Image sensor 132 can generate image signals in the form of analog voltages representative of light incident on each pixel of the image sensor. Referring to further aspects of head assembly 114, image sensor 132 can be controlled to clock out image signals from image sensor 132. Analog voltages representative of light incident on the various pixels of image sensor 132 can be propagated through signal conditioning circuit 136 along a cable, e.g., a coaxial cable disposed within elongated inspection tube 112. Head assembly 114 can include signal conditioning circuit 136 which conditions analog image signals for input to cable 138 and receives timing and control signals for control of image sensor 132. Image sensor 132 and signal conditioning circuit 136 can be disposed on a circuit board 139.

In the embodiment of FIG. 1, a head assembly of apparatus 100 at a distal end of inspection tube 112 comprises image sensor 132. Image sensor 132 of inspection apparatus 100 can, in one alternative embodiment, be located at a position spaced apart from head assembly 114 and disposed at a position rearward of a proximal end of inspection tube 112.

Figure 2:
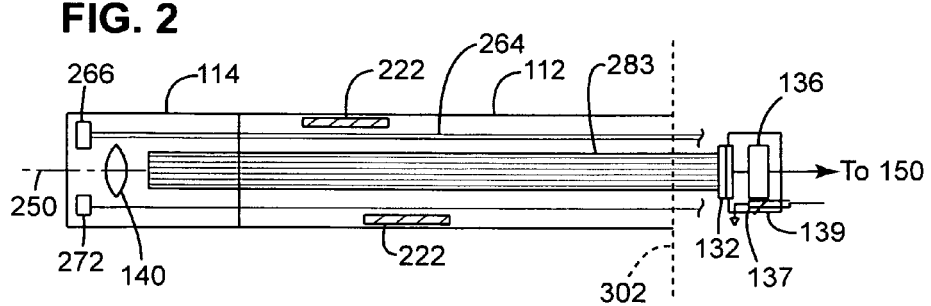
FIG. 2 is a block diagram illustrating an inspection apparatus in one embodiment.

Referring to FIG. 2, an imaging system fiber optic bundle 283 can be disposed in inspection tube 112, and can terminate in head assembly 114. The apparatus can be configured so that such a fiber optic bundle relays image forming light rays from head assembly 114 to the spaced apart image sensor spaced apart from head assembly 114. An example of such an embodiment is illustrated in FIG. 2. In the embodiment of FIG. 2, imaging lens 140 can focus an image of a target onto fiber optic bundle 283, which relays image forming light rays to image sensor 132 which in the embodiment of FIG. 2 is disposed at base assembly 302 spaced apart from head assembly 114. Inspection apparatus having fiber optic bundles for relaying image framing light rays are sometimes referred to as "fiberscopes." Inspection apparatus 100 can have an imaging axis 250 extending outwardly from head assembly 114.

Various circuits disposed at a position spaced apart from camera head assembly 114 can receive and process image signals generated by image sensor 132. Circuits for processing image signals generated by image sensor 132 can be disposed in base assembly 302. In the exemplary embodiment of FIG. 1, analog front end circuit 150 can include an analog gain circuit, an analog-to-digital converter, and a correlated double sampler and can receive analog image signals, digitize such signals and transmit digitized image signals to digital signal processor 152 (DSP). DSP 152, in the embodiment shown, can be configured to perform such processing tasks as color matrix processing, gamma processing, and can process digital image signals into a standardized video format, wherein video signals are expressed in a standardized data format. By way of example, video signals output by DSP 152 can be in a BT656 video format and data carried in the video signal can have a 422YCRCB data format. DSP 152 can be in communication with a random access memory 160 through system bus 158. Referring to further aspects of an electrical circuit for inspection apparatus 100, apparatus 100 can include timing generator circuit 156 which can send timing and control signals to signal conditioning circuit 136 for input to image sensor 132 as well as to analog front end circuit 150 and DSP 152. As indicated by communication line labeled "to 136," timing generator circuit 156 can send control signals such as exposure timing signals and frame rate timing signals to circuit 136 for input to image sensor 132. Timing generator circuit 156 can also generate illumination control signals for control of light source banks of apparatus 100. In some embodiments, DSP 152 can be configured to process image data, and can further be configured to send imaging parameter (e.g., exposure, illumination) control signals to timing generator circuit 156, which results in timing generator circuit 156 generating imaging parameter control signals for input to another component, e.g., circuit 136, or a regulator. In one embodiment, analog circuit front end circuit 150, DSP 152, and timing generator circuit 156 can be provided on separate integrated circuits (ICs). In one embodiment, analog front end circuit 150, DSP 152, and timing generator circuit 156 are provided as part of commercially available chips, e.g., an 814612 DSP chipset of the type available from SONY.

Referring to further aspects of apparatus 100, apparatus 100 can include DSP 180. DSP 180 can receive the formatted video output from DSP 152 for further processing. DSP 180 can be configured to perform a variety of processing tasks such as frame averaging, scaling, zoom, overlaying, merging, image capture, flipping, image enhancement and distortion correction. In one embodiment, DSP 180 can be provided by a TMS320DM642 Video/Imaging Fixed-Point Digital Signal Processor of the type available from TEXAS INSTRUMENTS. DSP 180 can be in communication with a volatile memory 161, e.g., a RAM, a non-volatile memory 162, and storage memory device 164. Non-volatile memory 162 shown as being provided by an EPROM memory device can also be provided by, e.g., an EEPROM memory device or an EPROM memory device. Software for operating apparatus 100 can be saved in non-volatile memory 162 when apparatus 100 is not operating and loaded into RAM 161 when operation of apparatus 100 is activated. Apparatus 100 can include other types of storage memory. For example, a USB "thumb drive" can be plugged into serial I/O interface 173. A Compact Flash memory card can be plugged into parallel I/O interface 174. A memory of apparatus 100 can be regarded as including memory 160, 161, 162, and 164, other storage memory, as well as internal buffer memories of DSP 152 and 180. Storage memory device 164 can be, e.g., a hard drive or removable disk. RAM 161, non-volatile memory 162, and storage device 164 can be in communication with DSP 180 via system bus 159. While DSP 152 and DSP 180 are shown as being provided on separate integrated circuits, the circuits of DSP 152 and DSP 180 could be provided on a single integrated circuit. Also, the functionalities provided by DSP 152 and DSP 180 could be provided by a general purpose microprocessor IC.

Referring to further circuit components of the block diagram of FIG. 1, apparatus 100 can further include display 210, keyboard 214, and joystick 218, each of which can be interfaced to DSP 180. Display 210, keyboard 214 and joystick 218 form a user interface of apparatus 100 in one embodiment. Keyboard 214 enables a user to initiate various control signals for the control of apparatus 100. Display 210 enables display of live video streaming images and other images to an inspector. For example, apparatus 100 can be controlled to switch from a live streaming video mode in which a live streaming video is being displayed to a mode in which a still image is displayed on display 210. Apparatus 100 can be configured so that apparatus 100 can generate user-initiated image retention control signals. Apparatus 100 can be configured so that an inspector can initiate a frame retention control signal by actuating a designated button of keyboard 214. Frame retention control signals can include, e.g., a freeze control signal, and a "take picture" control signal. Apparatus 100 can be configured so that when a freeze control signal is initiated, apparatus 100 repeatedly reads out to display 210 a frame of image data from a frame buffer. Apparatus 100 can be configured so that when a "take picture" control signal is initiated, apparatus 100 can save a frame of image data to non-volatile memory 162 and/or storage device 164.

In a further aspect, DSP 180 can be coupled to an I/O interface 172, e.g., an ETHERNET, USB interface enabling communication between apparatus 100 and an external computer. DSP 180 can also be coupled to one or more wireless communication interfaces 174, e.g., an IEEE 802.11 wireless transceiver and/or a Bluetooth wireless transceiver. DSP 180 can also be coupled to a parallel I/O interface 173, e.g., a Compact Flash and/or a PCMCIA interface. Apparatus 100 can be configured to send frames of image data saved in a memory thereof to an external computer and can further be configured to be responsive to requests for frames of image data saved in a memory device of apparatus 100. Apparatus 100 can incorporate a TCP/IP networking communication protocol stack and can be incorporated in a wide area network including a plurality of local and remote computers, each of the computers also incorporating a TCP/IP networking communication protocol stack.

Referring to further aspects of apparatus 100, apparatus 100 can include joystick 218 for controlling a positioning of head assembly 114. In one embodiment, articulation cables 222 can be incorporated in inspection tube 112 to enable movement of head assembly 114 into a desired position so that a field of view of apparatus 100 can be changed. Joystick 218 can be in communication with DSP 180. Apparatus 100 can be configured so that control signals for controlling movement (articulation) of head assembly 114 are initiated by manipulating joystick 218. Apparatus 100 can be configured so that when joystick 218 is moved, DSP 180 receives a control signal from joystick 218 and sends corresponding motor control signals to articulation motor 220 to produce a desired movement of head assembly 114.

In another aspect, inspection apparatus 100 can include a power supply circuit 251. Power supply circuit 251 can be interfaced to various alternative power sources e.g., serial I/O power source 254, AC/DC transformer source 256 and rechargeable battery 258.

Regarding an illumination assembly of inspection apparatus 100, an illumination assembly of inspection apparatus in one embodiment can include a first light source bank 262 and a second light source bank 272. Each light source bank can include one or more light sources. The one or more light sources of each bank can include one or more light emitting diodes (LEDs) such as white LEDs. In another embodiment, the one or more light sources of each light source bank can also include one or more laser diode assemblies. LEDs and laser diode assemblies can be regarded as solid state light sources. First light source bank 262 can be disposed in base assembly 302 spaced apart from head assembly 114 and second light source bank 272 can be disposed in head assembly 114. A fiber optic bundle 264 can be disposed in elongated inspection tube 112 for conducting light from first bank 262 through elongated inspection tube 112 and outwardly from head assembly 114 to illuminate a target. A diffuser 266 can be provided for diffusing light emitted through fiber optic bundle 264. While an embodiment having first and second light source bank is shown in FIG. 1, apparatus 100 in another embodiment can comprise only first light source bank 262. In another embodiment, apparatus 100 can comprise only light source bank 272. In another embodiment, the one or more light sources of each light source bank 262, 272 can be provided by one or more arc lamps.

In a further aspect of inspection apparatus 100, inspection apparatus 100 can include regulator 268 and regulator 278, each of which is coupled to power supply circuit 251. A light source bank driver signal output by regulator 268 can be varied to vary the duty cycle and/or the peak power supplied to first light source bank 262 and a driver signal output by regulator 278 can be varied to vary the duty cycle and/or peak power supplied to second bank light source 272. As will be described more fully herein, apparatus 100 in various embodiments can be configured so that DSP 152 or DSP 180, in response to receipt of various information such as image information and/or thermal information can generate various illumination control signals for control of the illumination assembly of apparatus 100. Such control signals in one embodiment can be received by timing generator circuit 156 by way of the communication line shown, and timing generator circuit 156 can responsively communicate appropriate illumination control signals to regulator 268 and/or regulator 278. Regulators 268 and 278 in turn can output light source driver signals. In any of the embodiments described herein, an illumination control signal generated by DSP 152 or DSP 180 can be generated so that a peak power level or duty cycle varies depending on a detected brightness of captured image data captured by apparatus 100. Apparatus 100 can be adapted so that DSP 152 or DSP 180 captures frames of image data and examines such frames for purposes of determining a brightness parameter. Where a brightness of a current frame decreases relative to a previously examined frame, an illumination control signal can be generated to provide a light source bank driver signal having one of an increased peak power level and an increased duty cycle. Where a brightness of a current frame increases relative to a previously examined frame, an illumination control signal can be generated to provide a light source bank driver signal having at least one of a reduced peak power level or reduced duty cycle. Apparatus 100 can be configured so that an illumination control signal can be varied to provide light source bank driver signals having such characteristics as to maintain a brightness of captured image data above a brightness threshold. If ambient light conditions are such that brightness is above a threshold without maximum peak power and maximum duty cycle, the peak power level and/or duty cycle can be reduced. If target reflection conditions are such that a brightness threshold is not achieved despite maximum peak power, maximum duty cycle light source bank driver signals, an illumination control signal can be generated to maintain a light source bank driver signal at a maximum peak power, maximum (full) duty cycle level.

Aspects of inspection apparatus 100 in various embodiments are now described in greater detail. In one embodiment apparatus 100 includes light source bank 262 disposed at a position spaced apart from head assembly 114. Light source bank 262 can comprise one or more LEDs. By providing light source bank 262 at a position spaced apart from head assembly 114 where image sensor 132 is disposed in head assembly 114, heat that is transferred to image sensor 132 from a light source bank of apparatus 100 is reduced. The heat control provided by disposing a light source bank at a position spaced apart from image sensor 132 can be enhanced by incorporating in apparatus 100 a brightness based illumination control as described herein previously, wherein a light source bank driver signal is varied responsively to a detected brightness of a captured image in such a manner that if brightness above threshold brightness can be provided without a maximum peak power and full duty cycle light source bank driver signal, the peak power and/or duty cycle of the light source driver signal can be reduced.

In another embodiment as alluded to previously, apparatus 100 can have two spaced apart light source banks; namely, a first light source bank 262 disposed at a position spaced apart from head assembly 114 and a second light source bank 272 disposed in head assembly 114. First light source bank 262 as indicated in FIG. 1 can direct light through fiber optic bundle 264 disposed within elongated inspection tube 112 and fiber optic bundle 264 can conduct the light thorough inspection tube 112 so that it is projected outwardly from head assembly 114 toward a target. In one embodiment, apparatus 100 can be configured to energize second light source bank 272 only on an "as needed" basis. In other words, apparatus 100 can be configured to have a first, "standard" operating mode in which only first spaced apart light source bank 262 is energized and second light source bank 272 is de-energized. Apparatus 100 can be configured to automatically switch out of the first operating mode and into a second operating mode on the sensing of sensed condition. In the second operating mode second light source bank 272 can be energized together with first light source bank 262. In one embodiment, apparatus 100 can be configured to switch out of the first operating mode and into the second operating mode on the condition that a brightness of a captured frame of image data has been determined to have fallen below a threshold brightness level. A brightness of captured frame of image data will vary depending on reflectivity conditions of a target and on ambient light conditions. For example, where a target is provided by a light color close range substrate, brightness of a captured image can be expected to be relatively high. However, where a head assembly of apparatus 100 is directed so that a field of view of apparatus 100 encompasses a far range substrate within a dark tunnel, a brightness of a captured frame of image data can be expected to be relatively low. Apparatus 100 can be configured so that second light source bank 272 is energized conditionally on the condition that brightness of a captured frame of image data falls below a threshold brightness, which threshold may be a predetermined threshold. In such manner, by energizing second light source bank 272 conditionally on the condition of a certain condition being sensed the apparatus is enabled to operate in an expanded range of brightness conditions, with an amount of heat delivered to image sensor 132 by proximately located light source bank 272 being conserved.

Figure 3:
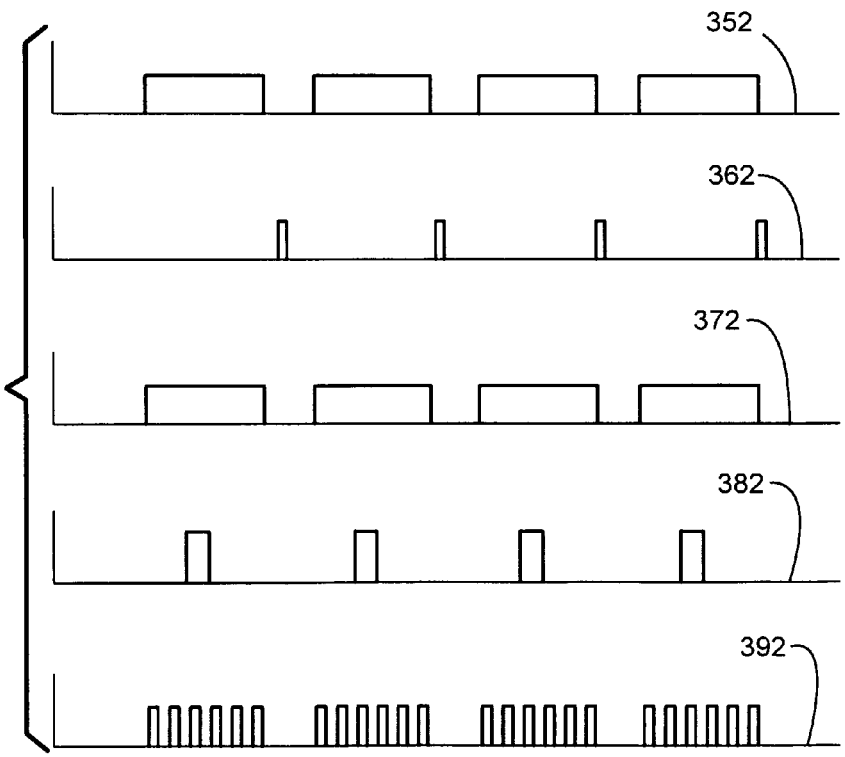
FIG. 3 is a timeline illustrating methods for controlling an inspection apparatus illumination assembly.

Referring to the timing diagram of FIG. 3, additional control functionality can be incorporated in inspection apparatuses for purposes of reducing an amount of heat delivered to electrical components of apparatus 100 by light sources and for further purposes of power conservation and reduced noise in a video signal.

Referring to the timing diagram of FIG. 3, timeline 352 shows an exposure control signal and timeline 362 shows a readout control signal. Such control signals can be generated by timing generator circuit 156. During the ON periods of the exposure control signal, pixels of image sensor 132 can be exposed to light. During an exposure period of image sensor 132, charges can build up on individual pixels of image sensor 132. Each exposure period can be followed by a readout control pulse. A readout control pulse can be provided by the readout control signal shown in timeline 362 switching to an ON state. When a readout control signal switches to an ON state, accumulated charges accumulating during the most recent exposure period are read out of image sensor.

While timeline 352 and timeline 362 illustrate that an exposure control signal and a readout control signal can be coordinated, apparatus 100 can be configured so that a light source bank driver signal can be coordinated with an exposure control signal. Referring to timeline 372, a light source bank driver signal for controlling energizing a light source or sources on an inspection apparatus illumination assembly is shown. Apparatus 100 can be configured so that each light source of an inspection apparatus illumination assembly is energized when the light source bank driver signal, as shown in timeline 372 is in an ON state and each light source of an inspection apparatus illumination assembly is de-energized when the light source bank driver signal, as shown in signal timeline 372 is in an OFF state.

It is seen from the timing diagram of FIG. 3 that the light source bank driver signal shown in timeline 372 can be coordinated with an exposure control signal. It is seen with reference to FIG. 3 that each light source of inspection apparatus 100 can be selectively energized on only during exposure periods of image sensor 132. By selectively energizing each light source of inspection apparatus 100 on only during exposure period, heat generated by the apparatus's illumination assembly can be reduced. Power consumption of apparatus 100 is also reduced, extending battery life of apparatus 100 where powered by a battery 258. While controlling illumination according to the timing diagram of FIG. 3 can be expected to bring about a reduction in generated heat and a reduction of power consumption, it should be noted that such reductions can be realized without affecting performance of apparatus 100. With the exposure control signal as shown by timeline 352 coordinated with the light source bank driver signal as shown by timeline 372, such that each light source of apparatus 100 can be energized selectively during exposure periods, energy can be conserved without negatively affecting the signal to noise ratio in captured frames of image data captured by apparatus 100.

In still another aspect, a light source driver signal of apparatus 100 can be thermally regulated. Referring again to FIG. 1, a thermistor 137 can be disposed in head assembly 114 proximate image sensor 132. Thermistor 137 can be disposed in such position in head assembly 114 as to sense a temperature of image sensor 132. Referring to FIG. 1, a voltage output varying in response to a change in resistance of thermistor 137 can be input into analog to digital converter 292 which digitizes the voltage reading and inputs the digitized information into DSP 180 for processing by DSP 180. DSP 180 can be configured to vary a driver signal controlling illumination control signal responsively to sensed temperature of image sensor 132. In one embodiment, apparatus 100 can be configured to reduce at least one of a peak power level and/or a duty cycle of light source bank driver signal driving light source bank 272 responsively to a sensed temperature of image sensor 132 exceeding a threshold temperature. In such manner, heat that is generated by light source bank 272 can be reduced responsively to a determination that a temperature of image sensor 132 has reached a level wherein performance of image sensor 132 can be expected to decline or has reached a level posing a risk to the expected life span of continued operation of image sensor 132. With heat that is generated by light source bank 272 reduced or eliminated, the temperature of image sensor 132 can be expected to fall back to a safe operating level. Referring again to the timing diagram of FIG. 3, timeline 392 shows a reduced duty cycle a light source bank driver signal. Relative to the control signal of timeline 372, a light source bank driver signal of timeline 392 has a reduced on time duty cycle, resulting in reduced heat generation and reduced power consumption relative the a light source bank driver signal of the timeline 372. Apparatus 100 can be configured so that a light source bank driver signal switches from the form shown in timeline 372 to the form of timeline 392 when a temperature of image sensor 132 is determined to have exceeded a threshold (e.g., a predetermined threshold).

A thermistor for sensing a temperature of an image sensor 132 or other component can be disposed at a location other than head assembly 114. For example, in the embodiment of FIG. 2 a thermistor 137 as well as a proximately located image sensor 132 are disposed within base assembly 302.

While apparatus 100 in the embodiment of FIG. 1 has a dedicated temperature sensing device (provided by thermistor 137), apparatus 100 can be configured so that a temperature of image sensor 132 can be sensed by processing of image signals generated by image sensor 132. Prior to apparatus 100 being put into operation as an inspection apparatus, image sensor 132 can be subject to a calibration procedure wherein the effect of increasing temperature in image signals generated by image sensor 132 is observed. A temperature indicating "signature set" of characteristics at each of several temperature levels can be observed and DSP 152 or 180 can be configured to examine newly captured frames for the presence of such temperature indicating characteristics. In such manner, apparatus 100 can be configured to sense temperature of image sensor 132 and, therefore, of head assembly 114 by detecting characteristics of image signals generated by image sensor 132. Apparatus 100 can also be configured to sense a temperature of head assembly 114 by sensing a forward voltage across a bank of LEDs 262, 272 when energized at a particular operating current. The forward voltage across light source bank 262, 272, when provided by one or more LED or another at a given operating current will vary with temperature. Accordingly, the forward voltage is indicative of temperature in head assembly 114 and of image sensor 132. In one example, as will be described further herein the voltage signal across bank 262, 272 can be sensed by a regulator 268, 278 digitized by regulator 268, 278 and input into DSP 180. Apparatus 100 can be configured to process temperature information derived by sensing a forward voltage across bank 262, 272 or through image signal analysis for purposes of varying a light source bank driver signal in the same manner described relative to processing of temperature information received from a temperature sensing device.

The components of base assembly 302 as described in connection with FIG. 1 can be distributed into one or more separately movable physical modules. Referring to the embodiment of FIG. 4, the components of base assembly 302 are all incorporated into a handset 310, having a handset housing 311. Handset 310 can be configured to be a hand held handset 310 in the embodiment shown and can include a handle 312. As shown in the embodiment of FIG. 5, the components of base assembly 302 can be distributed into a handset module 310 having a handset housing 311, and a base unit 320 having a base unit housing 321. In the embodiment of FIG. 5, elongated inspection tube 112 can be interfaced to handset 310.

In the embodiment of FIG. 6, the components of base assembly 302 are also distributed into a handset 310 having housing 311 and a base unit 320 having housing 321, except that in the embodiment of FIG. 6, elongated inspection tube 112 is interfaced to base unit 320. Where the circuit components of base assembly 302 are distributed into separately moveable physical modules, serializer/de-serialized circuits can be provided to provide electrical communication between the various physical modules. Wireless communication transceivers, e.g., Bluetooth transceivers can also be incorporated in the various physical modules to provide electrical communication between the various physical modules.

Figure 7:
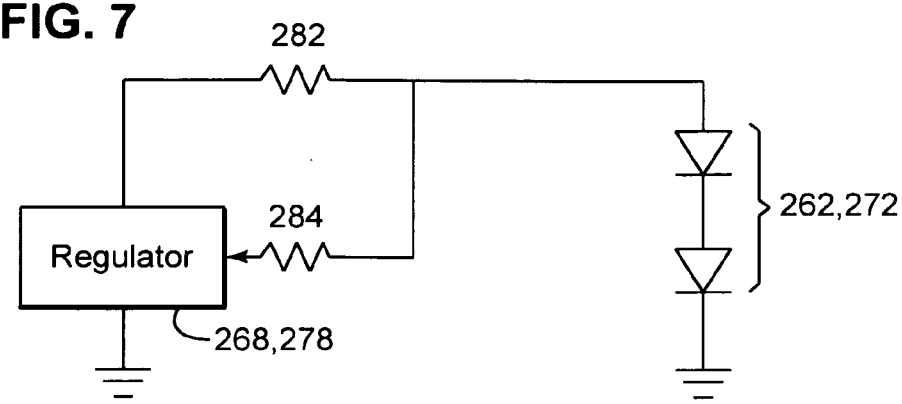
FIG. 7 is a circuit diagram of a regulator in one embodiment supplying power to a light source bank comprising a plurality of LEDs.
Figure 8:
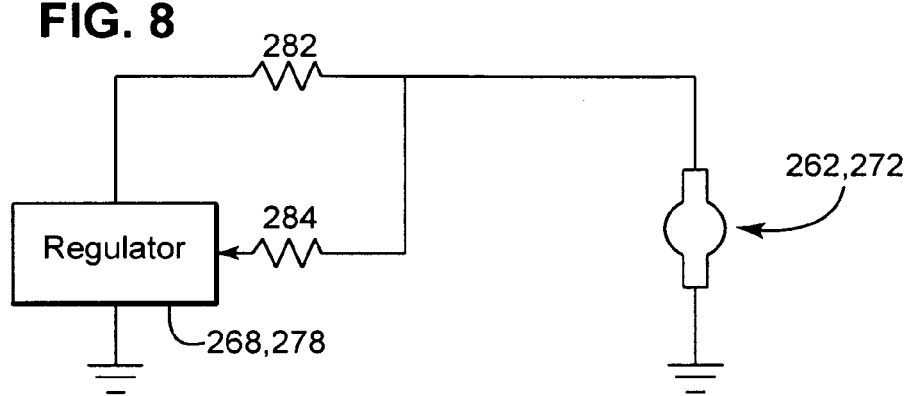
FIG. 8 is a circuit diagram of a regulator in one embodiment supplying power to a light source bank comprising an arc lamp.

In FIG. 7 there is shown an example of a regulator circuit including a regulator 268, 278 supplying power to a light source bank 262, 272 provided by a plurality of LEDs. In the example of FIG. 7, the regulator circuit shown can include a current sensing resistor 282 and a voltage sensing resistor 284. The value of resistor 282 is selected to be very small, and the value of resistor 284 is selected to be very large. Accordingly, substantially the current passing through light source bank 262, 272 passes through resistor 282. The value of resistor 282 is selected to cause a small voltage to develop across resistor 282 due to current passing through light source bank 262, 272. Regarding voltage sensing resistor 284, voltage sensing resistor 284 in the exemplary embodiment presents the voltage across a resistor 282 to a differential amplifier in regulator 268, 278, to sense the voltage across resistor 282, and by subtraction the voltage across light source bank 262, 272. Apparatus 100 can be configured so that regulator 268, 278 can output a light source bank driver signal to control current through light source bank 262, 272 responsively to a sensed voltage across light source bank 262, 272. Where light source bank 262, 272 is provided by one or more LEDs, the voltage across light source bank 262, 272 at a given supplied current will vary depending on the temperature of the light source bank. Accordingly, a forward voltage across bank 262, 272, a voltage that is sensed by regulator 268, 278 is indicative of and constitutes a measurement of the temperature of light source bank 262, 272. As indicated, a sensed voltage across bank 262, 272 can be sensed by regulator 268, 278 digitized by regulator 268, 278 and input to DSP 180. A forward voltage across light source bank when driven at a particular operating current is also indicative of bank temperature where the bank comprises other types of solid state light source e.g., one or more laser diode assemblies. In the example of FIG. 8 the regulator circuit has the same components as shown in FIG. 7 except that light source bank 262, 272 is provided by an arc lamp.

There is described herein an inspection apparatus configured so that a specialized operating mode can be initiated while the inspection apparatus outputs frames of image data to a display in forming a displayed live video streaming video image. An inspection apparatus can be configured so that the apparatus controls a light source bank driver signal responsively to a specialized operating mode being initiated. Specialized operating modes that can be initiated can include a boost mode, wherein a light source bank driver signal can be controlled to overdrive a light source bank for a limited period of time, a freeze frame mode wherein an inspection apparatus repeatedly outputs to a display a frame retained in a frame buffer, a strobe mode wherein an inspection apparatus can process image data to determine a parameter of a moving component represented in a frame of image data and can establish timing for a light source bank driver signal responsively to the processing, and an in-motion mode of operation, wherein a light source bank driver signal can be controlled so that an illumination on time pulse is narrowed for the time that the in-motion operating mode is active.

During operation to output a live streaming video image on display 210, incoming frames can be input into an input frame buffer of RAM 161, subject to processing by DSP 180 and output to an output frame buffer of RAM 161. Apparatus 100 can be configured so that when a freeze frame control signal is initiated, a frame retained in an output frame buffer is continually output to display 210. Apparatus 100 can also be configured so that when a save frame control signal is initiated, a frame presently retained in an input frame buffer is output to an addressable memory location of a memory device, e.g., RAM 161, non-volatile memory 162, or long term storage device 164.

Apparatus 100 can be configured so that various specialized operating modes can be initiated by an inspector during the time that apparatus 100 is outputting a live streaming video image. Apparatus 100 can output a live streaming video image by outputting successively captured frames to display 210. As has been indicated specialized operating modes can include a boost mode, wherein a light source bank can be overdriven for increasing lumens of light projected from apparatus 100 for a limited period of time, a freeze frame mode wherein the apparatus can repeatedly output to display 210 a frame of image data retained in a frame buffer, a strobe mode wherein the apparatus can establish a timing for a light source bank driver signal responsively to a processing of image data, and an in-motion mode wherein the inspection apparatus is utilized to capture in-motion frames of image data (frames representing scenes wherein the apparatus and/or an object within a field of view is in-motion).

By observing a live streaming video image, an inspector might determine that initiating a specialized operating mode would be desirable. In a boost mode as will be described herein, inspection apparatus 100 can overdrive a light source bank for a limited period of time for increasing lumens of light projected onto a target for a limited period of time. An inspector can determine that initiating a boost mode would be desirable if a live streaming video includes dark frames of image data in which details of frame are difficult to observe.

By observing a live streaming video image displayed on display 210 an inspector may determine that a displayed feature being displayed in a live streaming video image is of interest and therefore may determine that it would be desirable to "freeze" a frame of image data by initiating a freeze frame control signal for activation of a freeze frame mode of operation. Apparatus 100 can be configured so that when a freeze frame control signal is initiated to activate a freeze frame mode apparatus 100 ceases outputting successively captured frames to display 210 and commences repeatedly outputting the same frame to display 210. The same frame that is repeatedly output to display 210 can be a frame retained in a frame buffer of memory 161, e.g., an output frame buffer of memory 161. By observing a still frame displayed on display 210 an inspector can be expected to observe details of an image that an inspector would not be able to observe in the case a live streaming video image were being displayed via output of successively captured frames.

Also by observing a live streaming video image on display 210 an inspector may determine that a representation of an article having a repetitively moving component (e.g., a moving turbine, a fan) is being displayed on display 210. In another aspect apparatus 100 can be configured so that when observing a live streaming video image on display 210 representing an article having a repetitively moving component an inspector may initiate a strobe mode. Apparatus 100 can be configured so that when a strobe mode control signal is initiated to activate a strobe mode apparatus 100 can process frames of image data and responsively to the processing can establish a timing for a light source bank driver signal. Apparatus 100 can be configured so that when a strobe mode control signal is initiated apparatus 100 can output to a display 210 a live streaming video image corresponding to an article having a repetitively moving component in such manner that the live streaming video image has an appearance corresponding to a still article without moving components. Also by observing a live streaming video image, an inspector can determine that the apparatus or an object (e.g., an equipment article) represented in a field of view is in-motion and may accordingly determine that it would be advantageous to activate an in-motion mode of operation.

Figure 9:
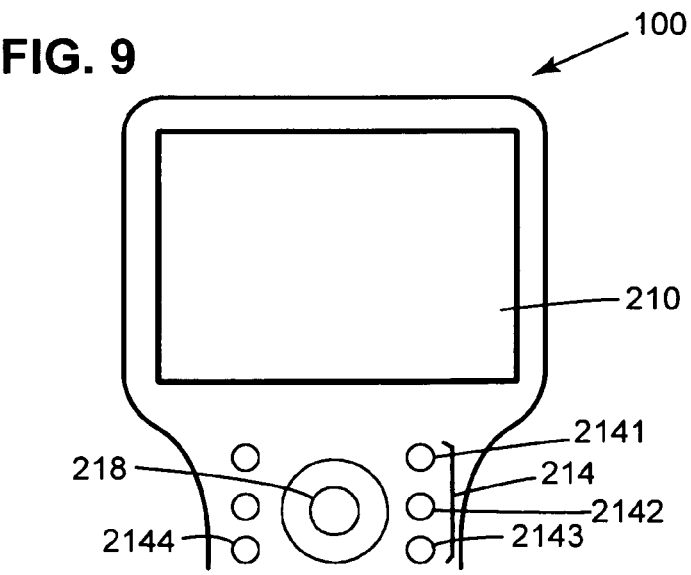
FIG. 9 is a diagram illustrating an exemplary user interface of an inspection apparatus.

Apparatus 100 can be configured so that an inspector can both activate and deactivate a specialized operating mode utilizing an actuator of a user interface of apparatus 100. Referring to FIG. 9 in one embodiment apparatus 100 can be configured so that by actuating button 2141 a boost mode control signal activating a boost mode is initiated, by actuating button 2142, a freeze frame mode control signal is initiated, by actuating button 2143 a strobe mode control signal is initiated activating a strobe mode, and by actuating button 2144 an in-motion mode control signal is initiated activating an in-motion mode. Apparatus 100 can be configured so that a mode selection control signal corresponding to a specialized mode remains active for as long as its corresponding button remains depressed and is deactivated to deactivate the specialized operating mode when its corresponding button is released. Apparatus 100 can be configured so that the exemplary mechanical buttons as shown in FIG. 9 are replaced or redundantly provided by virtual buttons displayed on display 210. Apparatus 100 can be configured so that control signals for activating a specialized operating mode can also be initiated automatically in response to a sensed condition, as will be described in great detail herein.

In embodiments having an available specialized operating mode selected from the group consisting of a boost mode a freeze frame mode and a strobe mode, apparatus 100 can have a single light source bank such as bank 272 disposed in head assembly 114, a single light source bank such as bank 262 disposed in base assembly 302, or a plurality of banks such as bank 272 and bank 262. Where apparatus 100 has more than one light source bank, a light source bank driver signal for driving each bank can be controlled responsively to a specialized operating mode being initiated and deactivated in a manner that is described herein. Where apparatus 100 has more than one light source bank (e.g., has bank 272 and bank 262), the same light source bank driver signal in one embodiment can be supplied to both banks simultaneously for driving of the banks 272, 262.

A boost mode is described in greater detail with reference to the timing diagram of FIG. 10 and the lookup table representation of FIG. 11. Prior to a boost mode control signal being initiated to activate a boost mode, a light source bank driver signal can have at least one of a baseline peak power level and a baseline duty cycle. The baseline peak power level can be a peak power level previously determined to be a peak power level which will not negatively impact performance of the driven light source bank (and/or proximately located electrical components) if driven at that level over a substantial period of time (e.g., for periods of one minute continuously or more). The baseline duty cycle similarly can be a duty cycle determined to be duty cycle which will not negatively impact performance of the driven light source bank (and/or proximately located electrical components) if the bank is driven at that duty cycle over a substantial period of time (e.g., for periods of one minute continuously or more).

Figure 10:
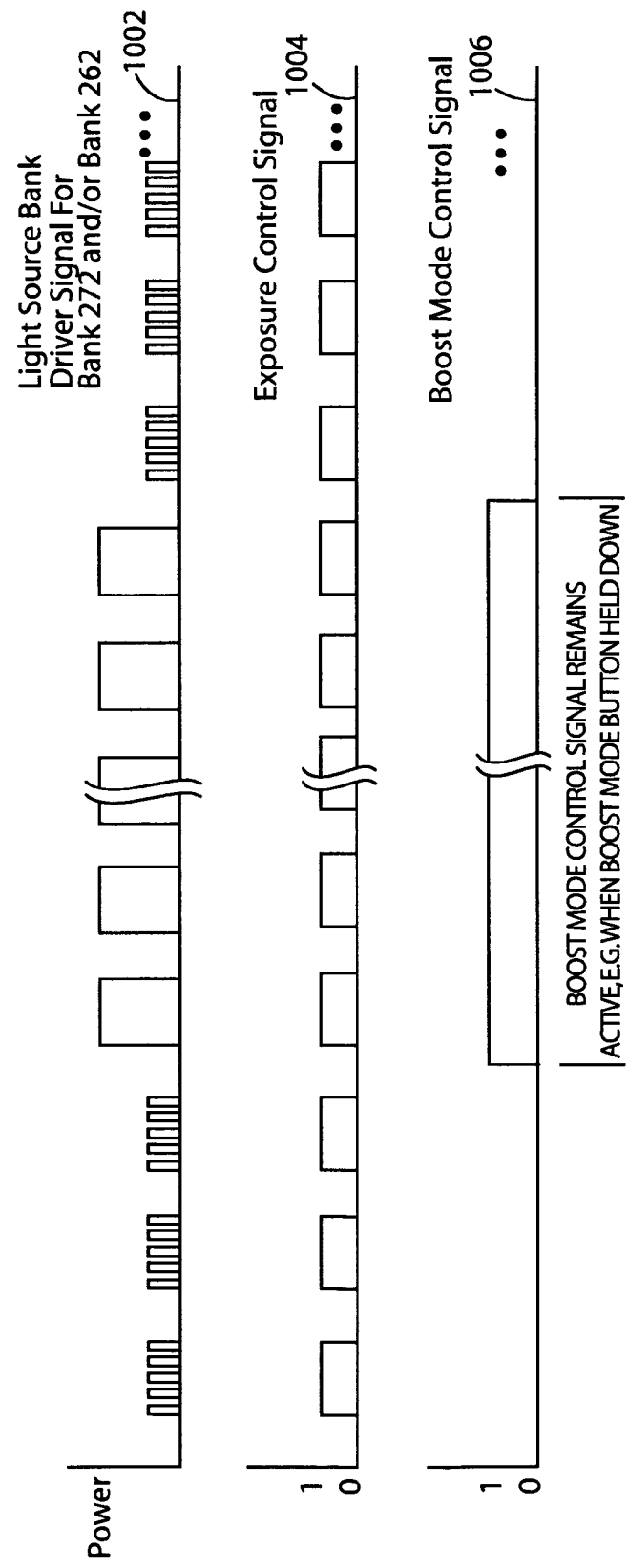
FIG. 10 is a timing diagram illustrating operation of an inspection apparatus in a boost mode of operation.

With further reference to the timing diagram of FIG. 10 a light source bank driver signal shown in timeline 1002 can have at least one of a higher than baseline peak power level and a higher than baseline duty cycle when a boost mode is made active. The light source bank driver signal can remain at the higher than baseline peak power and duty cycle levels for the time that apparatus 100 remains in the boost mode. As explained herein an inspector can initiate a boost mode control signal 1006 activating a boost mode by actuating a designated button 2141 and the boost mode control signal can remain active for the period that an inspector depresses the button. Apparatus 100 can be configured so that when an inspector releases a boost mode button 2141 a boost mode control signal 1006 can be deactivated to deactivate the boost mode. Apparatus 100 can be configured so that when a boost mode control signal 1006 is deactivated the light source bank driver signal 1002 can return to a baseline peak power level and a baseline duty cycle level. In the specific example of FIG. 10 a light source bank driver signal 1002 is coordinated with an exposure period control signal represented by timeline 1004; however, such coordination is not necessary for operation of a boost mode. In the specific example, the light source bank driver signal 1002 has a maximum (full) duty cycle during exposure periods when the boost mode is active, but has a less than maximum duty cycle during exposure periods when the boost mode is not active. When the boost mode is active captured frames of image data will normally be brighter, increasing the signal to noise ratio, and making finer details of captured frames perceivable by an inspector. With further reference to the timing diagram of FIG. 10 the peak power level of light source bank driver signal 1002 during a boost mode can be a peak power level previously determined to be a peak power level which could negatively impact performance of a driven light source bank (and/or its proximately located components) if a light source bank driven were driven at that level for a long duration (e.g., a period of more than one minute). The peak power level of light source bank driver signal can be a peak power level previously determined to a be a peak power level which will not negatively impact performance of the driven light bank (and or its proximately located components) if a light source bank were driven at that peak power level for a predetermined short duration (e.g., less than 10 seconds). Because apparatus 100 during a boost mode can drive a light source bank at a peak power level that could be unsafe if the signal were supplied for longer periods, apparatus 100 can be regarded to be "overdriving" a light source bank when operating in a boost mode. Tolerances of light sources and other components provided by component manufacturers can be consulted in determining the described baseline and boost mode peak power levels and duty cycles.

In one embodiment, apparatus 100 can be configured so that the boost mode after being made active (e.g., by actuating button 2141) is automatically deactivated after a timeout period. For example, it may be desirable to configure apparatus 100 so that apparatus 100 cannot operate in a boost mode for longer than a timeout period. The inventors observed that if apparatus 100 were always operated in boost mode for as long as an inspector depresses an actuator for activating mode, a light source bank could be overdriven for a long period of time negatively impacting a driven light source bank and potentially proximately located electrical components. Accordingly, in one embodiment apparatus 100 can be configured to automatically deactivate a boost mode after a timeout period irrespective of any action by an inspector to maintain a boost mode control signal in an active state. In one embodiment, the timeout period is a predetermined time period selected from an arbitrary group of short time periods (e.g., 5 sec., 10 sec. 20 sec.). In one aspect, a boost mode control signal controlling activation of a boost mode can be deactivated responsively either to an actuation (e.g., release) of a button by an inspector to deactivate the control signal or to an expiration of a timeout period.

In another embodiment the timeout period limiting the time that a boost mode can remain active is a period that is determined responsively to a sensor output. In one example, a timeout period limiting the time that a boost mode can remain active is determined by examining an output provided by a temperature sensor, such as a temperature sensor disposed in head assembly 114 or in base assembly 302. In one example a temperature sensor is provided by a light source bank 272, 262. Specifically, it has been explained herein that a voltage across a light source bank where provided by one or more LEDs or laser diode assemblies varies depending on the temperature of the light source bank. Accordingly, a temperature of a light source bank 272, 262 is indicated by a voltage across the light source bank. Further, a light source bank temperature provides an indication of a temperature of components proximate to the light source bank 272, 262.

Figure 11:
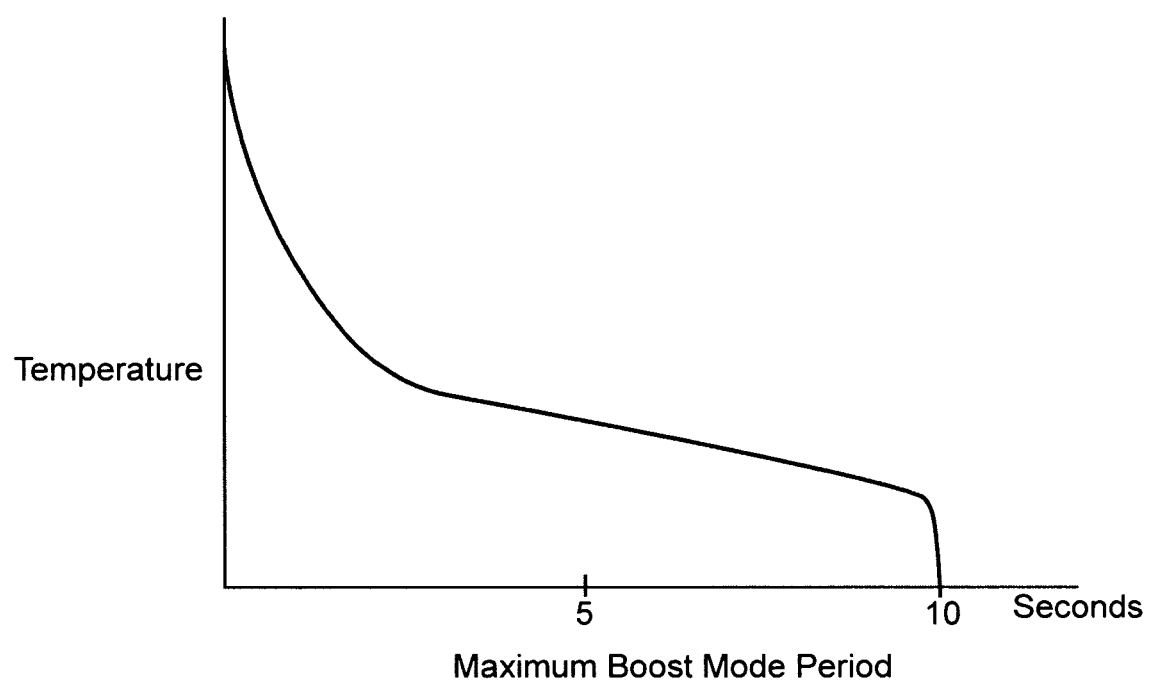
FIG. 11 is a representation of a lookup table for use in establishing a timeout period limiting a time at which an inspection apparatus can operate in a boost mode.

Referring to FIG. 11 a map representing a timeout period selection lookup table is shown. A timeout period limiting the time period which a boost mode can remain active can be determined by referencing the lookup table represented in FIG. 11. The temperature referenced in the lookup table represented in FIG. 11 can be a temperature reading provided by a voltage of a light source bank 272, 262, a temperature reading provided by processing image signals generated by image sensor 132 or a temperature reading provided by a thermistor 137. It is seen with reference to FIG. 11 that under cool "safe" temperatures a timeout period for a boost mode can be longer than under hotter temperatures. It is seen from the lookup table represented by table 11 that when hot temperatures are present above a predetermined temperature, a zero second timeout period is returned when the lookup table represented in FIG. 11 is referenced. Accordingly, it is seen that apparatus 100 can be configured so that under certain hot temperatures above a threshold, the boost mode can be disabled; that is, under hotter temperatures above a threshold, actuation of a boost mode actuator 2141 will have no effect and apparatus 100 will not be permitted to operate in a boost mode to overdrive a light source bank.

Figure 12:
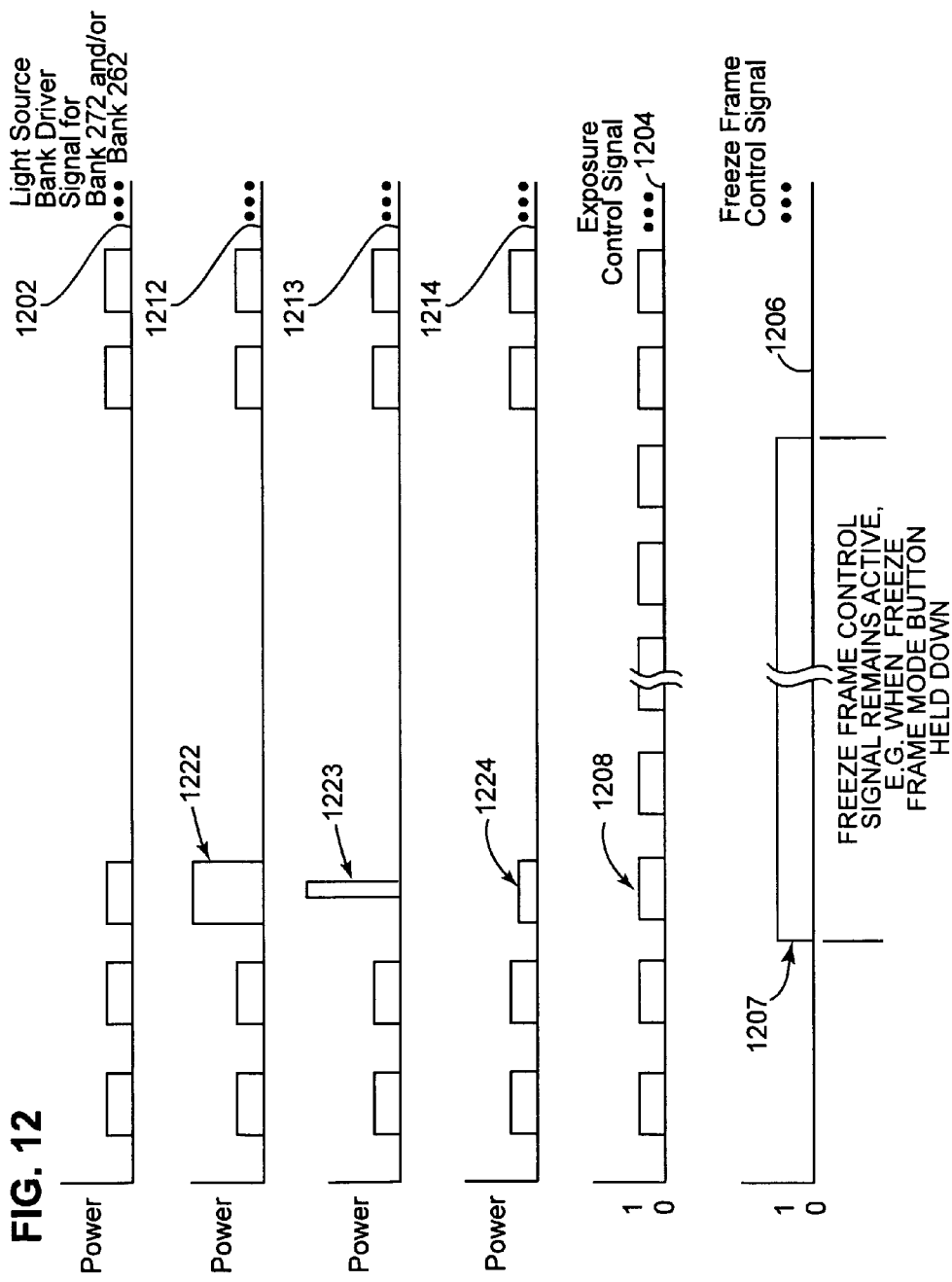
FIG. 12 is a timing diagram illustrating operation of an inspection apparatus in a freeze frame mode.

A freeze frame mode is described in further detail with reference to FIG. 12, showing a timing diagram illustrating options of apparatus 100 a freeze frame mode in an exemplary embodiment. Apparatus 100 can be configured so that when a freeze frame control signal 1206 is initiated and made active, apparatus 100 ceases outputting a live streaming video image on display 210 and commences outputting a still image on display 210. In outputting a still image, apparatus 100 can repeatedly output to display 210 a frame from a frame buffer of apparatus 100 which is continually over-written during the course of operation of apparatus 100 a live streaming video image. A frame buffer from which a frame is repeatedly output can be e.g., an output frame buffer of RAM 161. The inventors observed that while a previously captured still image is being displayed on display 210 during operation in a freeze frame mode, the displayed image on display 210 will not be affected by light projected by an illumination assembly of apparatus 100. Accordingly, the inventors determined that a light source bank can be de-energized during a time that a freeze frame mode of operation is active without impacting a displayed image on display 210. De-energizing a light source bank provides certain advantages. De-energizing a light source bank conserves power and allows a light source bank to cool, giving the light source bank time to "recover" if prior to the time the freeze frame mode is made active the light source bank exhibited a higher than desirable temperature. The timing diagram of FIG. 12 illustrates operation of an inspection apparatus 100 in a freeze frame mode. When a freeze frame mode control signal 1206 is initiated at time 1207 to make active a freeze frame mode, a light source bank driver signal given by timeline 1202 can be disabled to de-energize the light source bank (e.g., bank 272 and/or bank 262) for the time that the freeze frame operating mode remains active. When the freeze frame mode is deactivated (e.g., by releasing button 2142 in one example), the light source bank driver signal 1202 exhibits the characteristics exhibited by the driver signal 1202 prior to the time of initiation of the freeze frame control signal 1206 rendering active the freeze frame mode.

A freeze frame mode in various alternative embodiments is described with reference to timelines 1212, 1213, 1214, of FIG. 12 illustrating characteristics of a light source bank driver signal in various alternative embodiments. Referring to light source bank driver signal 1212, apparatus 100 can be configured so that subsequent to initiation of a light source bank driver signal at time 1207, a peak power level of light source bank driver signal 1207 is increased for a frame exposure period 1208, an exposure subsequent to time 1207, so that for period 1208 a peak power level of signal 1207 is increased relative to the baseline peak power level prior to time 1207. Further referring to the embodiment where a light source bank driver signal exhibits the characteristics of signal 1212, a frame that is repeatedly read out from a frame buffer after time 1207 can be the frame corresponding to exposure period 1208 exposed with a peak power level of signal 1212 increased relative to its baseline level prior to time 1207. With a peak power level of signal 1212 increased, a signal to noise ratio of the frame that is read out corresponding to period 1208 can be expected to be increased. In place of or in combination with increasing a peak power level as discussed in connection with signal 1212, apparatus 100 can be configured to increase a duty cycle of signal 1212 after time 1207 (if signal 1212 has a less that full duty cycle) responsively to initiation of a freeze frame control signal 1206. Signal 1212 can have certain characteristics like those of light source bank driver signal 1002 in a boost mode as described in connection with FIG. 10. Specifically, a peak power level for period 1208 can be a level previously determined to be level which could negatively impact performance of light source bank 262, 272 and/or proximately located computer. If bank 272, 262 were driven at such levels for a long duration (e.g., a period of more than one minute). Also, baseline peak power level of signal 1212 prior to time 1207 can be a level previously determined to be a peak power level which will not negatively impact performance of the driven light source bank (and/or proximate components) if driven at that level for a substantial period (e.g., for one minute or more continuously).

Referring to the exemplary light source bank driver signals of timeline 1213 and 1214, apparatus 100 can be configured so that an illumination on time pulse of a light source bank driver signal that is output during exposure period 1208 is determined responsively to a processing of image data. Referring to illumination on time pulse 1223 having a narrowed pulse width relative to a pulse width of signal 1213 prior to time 1207, illumination on time pulse width 1223 has characteristics advantageous for use in capturing a frame while apparatus 100 is in-motion relative to a scene (i.e., while apparatus is being moved and/or while objects represented in a field of view are in-motion). By narrowing a pulse width of signal 1213, effects of motion can be reduced. Referring to illumination on time pulse 1224, illumination on time pulse 1224 has characteristics advantageous for use in capturing a frame having represented therein an over-bloomed bright spot. Capturing frames of image data having over-bloomed bright spots is common where a field of view of apparatus 100 corresponds to a shiny (e.g., metal) surface which reflects light directed thereto substantially directly back to image sensor 132.

With further reference to timeline 1212, 1213, 1214, apparatus 100 can be configured so that apparatus 100 establishes an illumination on time pulse responsively to a processing of image data. Apparatus 100 can be configured to output an illumination on time pulse having an increased peak power level such as pulse 1222 where processing of image data indicates that image data is free of an over-bloomed bright spot and is not in-motion, to output a pulse having a narrowed pulse width such as pulse 1223 where processing of image data determines that an in-motion condition is present and to output a pulse having a decreased peak power level below a baseline level where processing of image data indicated that an over-bloomed bright spot is represented in a frame of image data. Apparatus 100 can be configured to determine that an over-bloomed bright spot is represented in a frame of image data if a grouping of pixel values corresponding to a grouping of pixel positions e.g., a 16×16 grouping are all at a peak or near peak value. Apparatus 100 can be configured so that whether pulse 1222, 1223, or 1224 is output after time 1207, the buffered frame of a frame buffer corresponding to exposure period 1208 under the specialized illumination condition is the frame that is repeatedly read out to display 210 subsequent to initiation of the freeze frame control signal 1206 at time 1207.

For reduction of processing requirements, accumulators can be utilized for determination of illumination on time pulse parameters that control characteristics of an illumination on time pulse to be output subsequent to initiation at a freeze frame control signal. So that a specialized illumination on time pulse can be output during the first frame exposure period after initiation of freeze frame control signal at time 1207, apparatus 100 can be configured so that illumination on time pulse parameters determining the characteristics of time pulse are determined based on processing of a frame or frames of image data having exposure periods of more than one exposure period prior to the time of initiation of signal 1206 at time 1207 (in one embodiment, apparatus 100 can be expected to have a processing lag time of more than one frame period).

Operation of an inspection apparatus 100 in a "strobe" mode is described with reference to the flow diagram of FIG. 13. An inspector may desire to initiate a strobe mode when an inspector is performing an inspection relating to an article having repetitively moving component (e.g., a fan or a turbine). When a strobe mode is made active, apparatus 100 can process image data to determine a timing of the moving component represented in the image data and can establish a timing for a light source bank driver signal responsively to the processing. When a strobe mode is made active a live streaming video image may be displayed on display 210 in such manner that a moving component has the appearance of still (non-moving) components.

Figure 13:
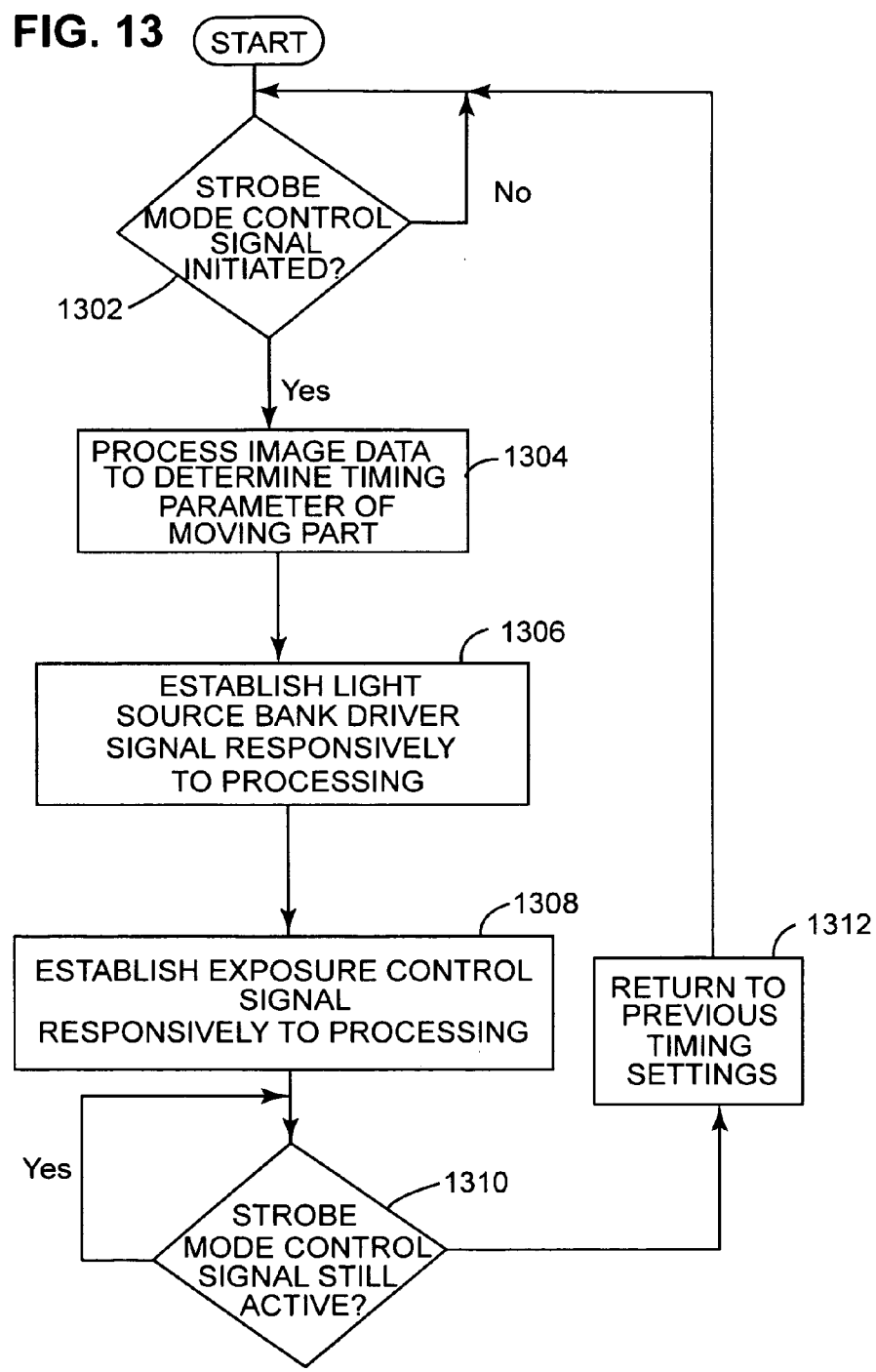
FIG. 13 is a flow diagram illustrating operation of an inspection apparatus in a strobe mode.

Referring to the flow diagram of FIG. 13 a strobe mode control signal may be initiated at block 1302. At block 1304 apparatus 100 can process image data to determine a timing parameter of a moving component represented in the processed image data. At block 1306 apparatus 100 can establish a light source bank driver signal timing responsively to the processing at block 1304 and at block 1308 apparatus 100 can optionally establish an exposure control signal responsively to the processing of block 1304. At block 1310 apparatus 100 can determine whether a strobe mode control signal has been de-activated (e.g., by releasing button 2143). If a strobe mode control signal has been de-activated apparatus 100 at block 1312 can return a timing of a light source bank driver signal to a timing prior to the time of initiation of the strobe mode. Also at block 1312 if a timing of an exposure control signal was changed for operation in the strobe mode a timing of an exposure control signal can be returned to a timing exhibited prior to the time of initiation of the strobe mode.

Figure 14:
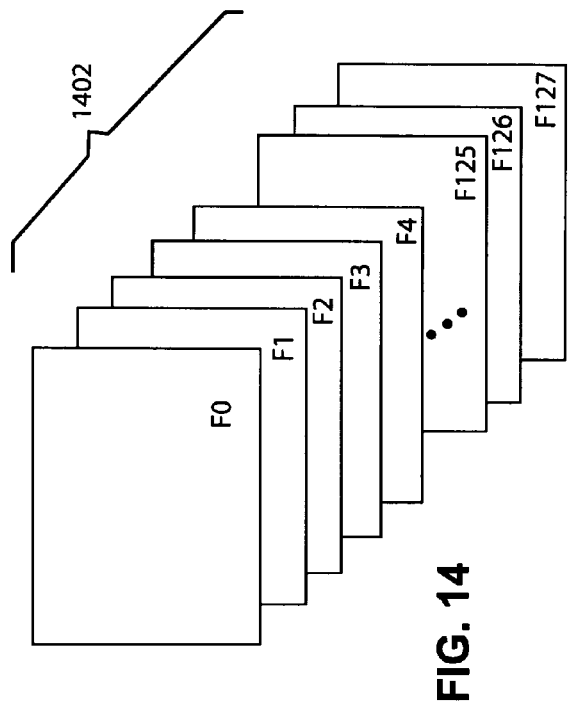
FIG. 14 is a representation of a set of frames which may be examined by an inspection apparatus in a strobe mode of operation.

In executing block 1304 apparatus 100, e.g., with use of DSP 180 can examine a set of frames 1402, e.g., a set of 128 frames, e.g., frames $F_0$-$F_{127}$ as shown in FIG. 14. Where apparatus 100 has a frame rate of 30 frames per second, 128 frames can be captured over a time of 4 seconds. In executing block 1304 a light source bank driver signal can be controlled to exhibit a narrow pulse width as shown by timeline 382 (FIG. 3) to reduce smearing in the representation of the moving component. In examining the set of frames 1402 apparatus 100 can identify matching frames of the set of frames 1402. Where the article having a moving component has a moving component moving at a constant frequency, examination of timestamps of the matching frames can yield a determination of the frequency with which the moving component is moving.

With a timing parameter (e.g., frequency) of a moving part determined, apparatus 100 can proceed to block 1306. At block 1306 apparatus 100 can establish a light source bank timing responsively to the processing at block 1304. At block 1306 apparatus 100 can establish a timing of a light source bank driver signal so that a frequency with which a pulse forming a light source bank driver signal is energized corresponds to (e.g., is equal to or is a multiple of) the frequency with which a moving component is moving as determined at block 1304. With a frequency of the light source bank driver signal synchronized with a frequency of moving component, a live streaming video image output by apparatus 100 on display 210 will have the appearance that an article having a still component is being represented even though the article has a moving component. In one embodiment block 1306 is executed to change a timing of a light source bank driver signal without changing a timing of an exposure control signal. In such an embodiment, frames captured without a light source bank being energized can be discarded in the process of outputting incoming frames for display on display 210.

In another embodiment, apparatus 100 executes block 1308 to establish a timing for an exposure control signal responsively to a timing of a moving component as determined at block 1304. At block 1308 apparatus 100 can establish a timing of an exposure control signal so that exposure periods have a frequency equal to a determined frequency of moving component as determined at block 1304. In executing block 1308 apparatus 100 can change a frame rate of image sensor 132.

At block 1310 apparatus 100 can determine whether a strobe mode control signal has been de-activating (e.g., by releasing button 2143). If a strobe mode control signal has been de-activated apparatus 100 at block 1312 can return a timing of a light source bank driver signal to a setting prior to the time of initiation of a strobe mode control signal actuating a strobe mode. Also at block 1312 if an exposure control signal timing was changed for operation in the strobe mode an exposure control signal timing can be returned to a timing exhibited prior to the time of initiation of a strobe mode control signal activating a strobe mode.

Figure 15:
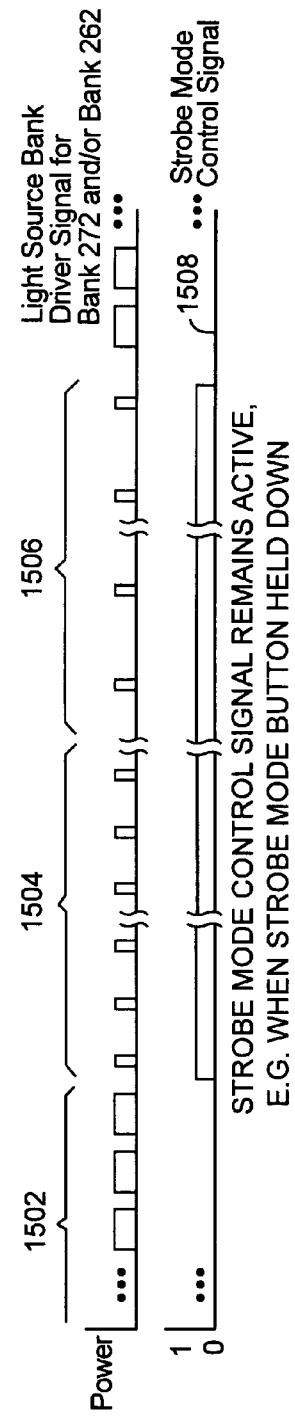
FIG. 15 is a timing diagram illustrating operation of an inspection apparatus in a strobe mode of operation.

A timing diagram illustrating operating of apparatus 100 in a strobe mode is shown in FIG. 15. At period 1502 prior to a time at which a strobe mode is activated by initiation of strobe mode control signal indicated by time line 1508, illumination on time pulses have a first pulse width which can substantially correspond to a pulse width of a corresponding exposure control signal. After a strobe mode has been made active, apparatus 100 can enter period 1504 during which time apparatus 100 processes image data to determine a timing parameter of a moving component represented in the processed image data. As indicated by period 1504, a pulse width of an illumination on time pulse forming a light source bank driver signal can be reduced when apparatus 100 first enters a strobe mode; however, a frequency of the illumination of the time pulse does not change at the image data processing stage (block 1304) of a strobe mode. After a timing parameter has been determined, apparatus 100 can enter period 1506, in which apparatus 100 establishes a new light source bank driver signal timing responsively to the image data processing at block 1304. As indicated by period 1506 apparatus 100 can change a frequency of an illumination on time pulse responsively to determining a frequency of moving component represented in image data as determined at block 1304.

In another aspect, apparatus 100 can be configured to have a specialized operating mode in which apparatus 100 is enabled to reduce the negative impact of motion on captured frames of image data. Prior to activation of an "in-motion" operating mode, while operating in what can be termed a "normal" operating mode, apparatus 100 can generate a light source bank driver signal as indicated by timeline 372 wherein an on period of a light source bank driver signal approximately corresponds to an on period of exposure. In a normal operating mode an on period of a light source bank driver signal can correspond to and be approximately as long in duration as an on period of exposure.

Referring to the timing diagram of FIG. 3, apparatus 100 can be configured so that when an "in-motion" mode of operation is made active, a light source bank driver signal energizing each light source of apparatus 100 can take on the characteristics shown in timeline 382. Comparing timeline 382 to timeline 372 it is seen that a pulse width of on time pulses of a light source bank driver signal can be reduced when an "in-motion" operating mode of apparatus 100 is made active. Referring to timeline 382, a light source bank driver signal remains coordinated with an exposure control signal so that each light source of apparatus 100 can be energized only during exposure periods. However, the on time of illumination is reduced as compared to the on time of illumination during a normal operation mode. With each light source of apparatus 100 being on for a shorter time during each exposure period of image sensor 132, higher quality frames of image data can be expected to be captured by apparatus 100 in substantial motion (in-motion) operating conditions. Referring to timelines 372 and 382, an on period of a light source bank driver signal can last by only a portion of an on period of exposure. In the example of FIG. 3 an on period of light source bank driver signal indicated by timeline 382 in an in-motion mode consumes less than half of an exposure period as indicated by timeline 372. With the pulse width of a light source bank driver signal being reduced, the amount of heat generated by each light source is reduced and power consumption is reduced.

Apparatus 100 can be configured so that a described specialized operating mode can be user selectable. For example, apparatus 100 can be configured so that when an inspector actuates one of the buttons 2141, 2142, 2143, 2144, apparatus 100 is driven from a normal operating mode to a specialized operating mode corresponding to the button. Accordingly, apparatus 100 can be configured in one embodiment so that a control signal corresponding to a described specialized operating mode is initiated made active responsively to an actuation of an actuator by an inspector.

In one embodiment, apparatus 100 can be configured so that a control signal corresponding to a described specialized operating mode can, in addition or in the alternative, be made active responsively to a sensed condition. For example, regarding the boost mode, apparatus 100 can be configured so that a boost mode control signal activating a boost mode is automatically initiated and therefore made active responsively to processing of incoming image data to determine a brightness of incoming image data. Regarding the freeze frame mode, apparatus 100 can be configured so that a freeze frame mode control signal activating a freeze frame mode is automatically initiated and made active responsively to a processing of incoming image data for recognizing of a predetermined recognizable object. For example, apparatus 100 in one embodiment can be configured to automatically activate a freeze frame mode when a predetermined recognizable object is recognized (e.g., a crack, an edge having certain characteristics). Regarding the strobe mode, apparatus 100 can be configured so that a strobe mode control signal activating a strobe mode is automatically initiated and made active responsively to a processing of incoming image data for detectors of an in-motion condition (detection of motion). Methods for detecting motion are described herein. Regarding an "in-motion" mode, apparatus 100 can be configured so that an in-motion control signal activating an in-motion mode is automatically initiated and made active responsively to a processing of image data for sensing motion. Apparatus 100 can be configured so that if processing of image data indicates that apparatus 100 is stopped then a "normal" mode is made active and when processing of image data indicates that apparatus 100 is in-motion, the in-motion mode is made active.

A number of algorithms can be employed for sensing motion. For example, apparatus 100 can be configured to determine that the apparatus is in-motion where subtracting of a second successive frame from a first successive frame yields a difference score above a threshold difference score. Where image sensor 132 is of a type that can output interlaced image signals in a first field and a second field motion can be indicated where subtracting the second field from the first field yields a difference score above a threshold difference score. It has been described that a strobe mode and an illumination mode control signal can be made active responsively to a sensing of motion. In one embodiment, where apparatus 100 is capable of operating in both a strobe mode and an in-motion mode apparatus 100 can be configured so that when motion is sensed, apparatus 100 initially activates a strobe mode and switches into an in-motion mode conditionally on the condition that apparatus 100 determines that there is no represented component represented in image data that is moving at a constant frequency. Where apparatus 100 is configured so that a control signal for activating a specialized operating mode is initiated responsively to a sensed condition, apparatus 100 can further be configured so that the control signal for activating the specialized operating mode remains in an active state (unless disabled by a superseding condition as in a boost mode time out) for as long as the sensed condition initiating the control signal remains sensed.

A small sample of the apparatuses described herein is as follows.

A1. An inspection apparatus for inspecting a target, said inspection apparatus comprising:
an elongated inspection tube;
a head assembly disposed at a distal end of said elongated inspection tube, said head assembly having an imaging lens;
an image sensor generating image signals representing said target;
a light source bank comprising at least one LED, said light source bank being disposed at a position spaced apart from said head assembly; and
a fiber optic bundle disposed in said elongated inspection tube and being arranged to conduct light from said light source bank and outwardly from said head assembly.

A2. The inspection apparatus of A1, wherein said light source bank comprises a plurality of LEDs.

A3. The inspection apparatus of A1, wherein said image sensor is disposed in said head assembly.

A4. The inspection apparatus of A1, wherein said image sensor is disposed in a location spaced apart from said head assembly.

B1. An inspection apparatus comprising:
an elongated inspection tube;
a head assembly disposed at a distal end of said elongated inspection tube, said head assembly having an imaging lens;
an image sensor generating image signals;
a first light source bank comprising at least one LED, said first light source bank being disposed at a position spaced apart from said camera head assembly;
a fiber optic bundle disposed in said elongated inspection tube and being arranged to conduct light from said light source bank and outwardly from said camera head assembly; and
a second light source bank disposed in said head assembly.

B2. The inspection apparatus of B1, wherein said inspection apparatus is configured to selectively energize said first bank without energizing said second bank until a brightness of a captured image falls below a threshold and, wherein said apparatus is configured to energize said second bank conditionally on the condition that said brightness falls below said threshold.

B3. The inspection apparatus of B1, wherein said image sensor is disposed in said head assembly.

B4. The inspection apparatus of 1, wherein said inspection apparatus is configured to sense a temperature of said apparatus and to output a light source bank driver signal responsively to said sensed temperature.

B5. The inspection apparatus of B1, wherein said inspection apparatus is configured to sense a temperature of said apparatus and to output a light source bank driver signal responsively to said sensed temperature, and wherein for sensing said temperature said apparatus senses a voltage across at least one of said first light source bank or said second light source bank.

B6. The inspection apparatus of B1, wherein said second light source bank comprises at least one LED.

B7. The inspection apparatus of B1, wherein said second light source bank comprises at least one laser diode assembly.

C1. An inspection apparatus comprising:
an elongated inspection tube;
a head assembly disposed at a distal end of said elongated inspection tube, said head assembly having an imaging lens;
an image sensor generating image signals;
at least one light source bank, wherein said light source bank comprises at least one LED;
wherein said apparatus is configured to send exposure control timing signals to said image sensor in such manner that said image sensor has exposure on periods and exposure off periods intermediate said exposure on periods; and
wherein said apparatus is further configured to output a light source bank driver signal for said at least one light source bank, and wherein said light source bank driver signal is coordinated with said exposure control timing signal such that said light source bank is energized during said exposure periods of said image sensor and de-energized during exposure off periods of said image sensor.

C2. The inspection apparatus of C1, wherein said at least one light source bank is disposed in said head assembly.

C3. The inspection apparatus of C1, wherein said inspection apparatus includes a base assembly disposed at a proximal end of said elongated inspection tube, wherein said at least one light source bank is disposed in said base assembly.

C4. The inspection apparatus of C1, wherein said inspection apparatus is configured so that said light source bank driver signal driver said at least one light source bank at less than a maximum duty cycle during said exposure periods.

D1. An inspection apparatus comprising:
an elongated inspection tube;

a head assembly disposed at a distal end of said elongated inspection tube, said head assembly having an imaging lens,
an image sensor generating image signals;
at least one light source bank;
wherein said inspection apparatus is configured to output a light source bank driver signal for driving said at least one light source bank;
wherein said inspection apparatus is configured to sense a brightness of said image signals; and
wherein said inspection apparatus adjusts said light source bank driver signal for driving at least one light source bank responsively to said brightness.

D2. The inspection apparatus of D1, wherein said inspection apparatus in adjusting said light source bank driver signal adjusts a peak power level of said light source bank driver signal.

D3. The inspection apparatus of D1, wherein said inspection apparatus in adjusting said light source bank driver signal adjusts a duty cycle of said light source bank driver signal.

D4. The inspection apparatus of D1, wherein said at least one light source bank comprises a single LED.

D5. The inspection apparatus of D1, wherein said at least one light source bank comprises a plurality of LEDs.

D6. The inspection apparatus of D1, wherein said at least one light source bank includes a first light source bank disposed at a location spaced apart from said head assembly and a second light source bank disposed in said head assembly.

D7. The inspection apparatus of D1, wherein said at least one light source bank includes a first light source bank disposed at a location spaced apart from said head assembly and a second light source bank disposed in said head assembly, wherein said inspection apparatus is configured to energize said second light source bank conditionally on the condition that said brightness falls below a threshold brightness.

E1. An inspection apparatus comprising:
an elongated inspection tube;
a head assembly disposed at a distal end of said elongated inspection tube, said head assembly having an imaging lens,
an image sensor generating image signals;
at least one light source bank;
wherein said inspection apparatus is adapted to output a light source bank driver signal for driving said light source bank;
wherein said inspection apparatus is adapted to sense a temperature of said image sensor; and
wherein said inspection apparatus adjusts said light source bank driver signal for driving at least one light source bank responsively to said temperature of said image sensor sensed by said inspection apparatus.

E2. The inspection apparatus of E1, wherein said inspection apparatus includes a thermistor disposed proximate said image sensor, and wherein said inspection apparatus is configured so that in sensing a temperature of said image sensor, said inspection apparatus reads an output of said thermistor.

E3. The inspection apparatus of E1, wherein said inspection apparatus in sensing a temperature of said image sensor processes said image signals.

E4. The inspection apparatus of E1, wherein said at least one light source bank is disposed proximate said image sensor, and wherein said inspection apparatus in sensing said temperature senses a voltage across said light source bank.

AA1. An inspection apparatus comprising:
an elongated inspection tube;
a head assembly disposed at a distal end of said elongated inspection tube;
a two dimensional image sensor generating image signals;
a base assembly disposed at a proximal end of said elongated inspection tube;
a display disposed on said base assembly;
at least one light source bank for outputting light that is projected outwardly from said head assembly;
wherein said inspection apparatus is configured to output to said display a live streaming video image;
wherein said inspection apparatus is configured so that a control signal for activating a specialized operating mode can be initiated responsively to an actuation of actuator by an inspector at a time at which said inspection apparatus outputs to said display said live streaming video image, the specialized operating mode being selected from the group consisting of a boost mode, a freeze frame mode, a strobe mode and an in-motion mode; and
wherein said inspection apparatus is further configured so that said apparatus changes a light source bank driver signal driving said at least one light source bank responsively to said control signal being initiated.

AA2. The inspection apparatus of AA1, wherein said apparatus changes a peak power level of said light source bank driver signal responsively to said control signal being initiated.

AA3. The inspection apparatus of AA1, wherein said apparatus changes a duty cycle of said light source bank driver signal responsively to said control signal being initiated.

AA4. The inspection apparatus of AA1, wherein said apparatus changes an illumination on time pulse width of said light source bank driver signal responsively to said control signal being initiated.

AA5. The inspection apparatus of AA1, wherein said apparatus changes a frequency of an illumination on time pulse forming said light source bank driver signal responsively to said control signal being initiated.

AA6. The inspection apparatus of AA1, wherein said apparatus disables said light source bank driver signal responsively to said control signal being initiated.

AA7. The inspection apparatus of AA1, wherein said at least one light source bank includes a light source bank disposed in said head assembly.

AA8. The inspection apparatus of AA1, wherein said at least one light source bank includes a light source bank disposed in said base assembly.

AA9. The inspection apparatus of AA1, wherein said at least one light source bank comprises at least one LED.

AA10. The inspection apparatus of AA1, wherein said at least one light source bank comprises at least one laser diode assembly.

BB1. An inspection apparatus comprising:
an elongated inspection tube;
a head assembly disposed at a distal end of said elongated inspection tube;
a two dimensional image sensor generating image signals;
a base assembly disposed at a proximal end of said elongated inspection tube;
a display disposed on said base assembly;
at least one light source bank for outputting light that is projected outwardly from said head assembly;
wherein said inspection apparatus is configured to output on said display a live streaming video image;
wherein said inspection apparatus is configured so that a boost mode control signal for activating a boost mode can be initiated at a time at which said inspection apparatus outputs to said display said live streaming video image;
wherein said inspection apparatus is further configured so that said apparatus increases at least one of a peak power level and a duty cycle of a light source bank driver signal for driving said at least one light source bank when said boost mode control signal is initiated.

BB2. The inspection apparatus of BB1, wherein said inspection apparatus is configured so that said boost mode control signal can be initiated responsively to an actuation of an actuator by an inspector.

BB3. The inspection apparatus of BB1, wherein said inspection apparatus is configured so that said boost mode control signal can be initiated responsively to sensing of a condition by said inspection apparatus.

BB4. The inspection apparatus of BB1, wherein said inspection apparatus is configured so that said boost mode control signal can be initiated responsively to an actuation of an actuator by an inspector or a sensing of a condition by said inspection apparatus.

BB5. The inspection apparatus of BB1, wherein said inspection apparatus is configured to automatically deactivate said boost mode after a timeout period.

BB6. The inspection apparatus of BB1, wherein said inspection apparatus is configured so that an inspector can deactivate said boost mode by actuation of an actuator.

BB7. The inspection apparatus of BB1, wherein said inspection apparatus is configured so that said inspection apparatus can deactivate said boost mode on the earliest occurrence of an action by an inspector to deactivate the boost mode or an expiration of timeout period.

BB8. The inspection apparatus of BB1, wherein said inspection apparatus is configured to automatically deactivate said boost mode after a timeout period, the timeout period being a predetermined period.

BB9. The inspection apparatus of BB1, wherein said inspection apparatus is configured to automatically deactivate said boost mode after a timeout period, the timeout period being determined responsively to a sensor output.

BB10. The inspection apparatus of BB1, wherein said inspection apparatus is configured to automatically deactivate said boost mode after a timeout period, the timeout period being determined responsively to a temperature sensor output.

BB11. The inspection apparatus of BB1, wherein said inspection apparatus is configured to automatically deactivate said boost mode after a timeout period, the timeout period being determined responsively to a temperature sensor output, wherein said temperature sensor is provided by said at least one light source bank.

BB12. The inspection apparatus of BB1, wherein said inspection apparatus is configured to automatically deactivate said boost mode after a timeout period, the timeout period being determined responsively to a temperature sensor output, wherein said temperature sensor is disposed in proximity with said light source bank.

BB13. The inspection apparatus of BB1, wherein said inspection apparatus increases a peak power level of said light source bank driver signal when said control signal is initiated.

BB14. The inspection apparatus of BB1, wherein said inspection apparatus increases a duty cycle of said light source bank driver signal when said control signal is initiated.

CC1. An inspection apparatus comprising:
an elongated inspection tube;
a head assembly disposed at a distal end of said elongated inspection tube;
a two dimensional image sensor generating image signals;
a base assembly disposed at a proximal end of said elongated inspection tube;
a display disposed on said base assembly;
at least one light source bank for outputting light that is projected outwardly from said head assembly;

wherein said inspection apparatus is configured to output on said display a live streaming video image;

wherein said inspection apparatus is configured so that a freeze frame mode control signal for activating a freeze frame mode can be initiated at a time at which said inspection apparatus outputs to said display said live streaming video image;

wherein said inspection apparatus is configured to repeatedly output to said display a frame of image data retained in a frame buffer when said freeze frame mode is active; and wherein said inspection apparatus is further configured so that said apparatus disables a light source bank driver signal for driving said at least one a light source bank when said freeze frame mode is active so that said light source bank is de-energized for at least a portion of a time period that said freeze frame mode remains active.

CC2. The inspection apparatus of CC1, wherein said inspection apparatus is configured so that said freeze frame mode control signal can be initiated responsively to an actuation of an actuator by an inspector.

CC3. The inspection apparatus of CC1, wherein said inspection apparatus is configured so that said freeze frame mode control signal can be initiated responsively to sensing of a condition by said inspection apparatus.

CC4. The inspection apparatus of CC1, wherein said inspection apparatus is configured so that said freeze frame mode control signal can be initiated responsively to an actuation of an actuator by an inspector or a sensing of a condition by said inspection apparatus.

CC5. The inspection apparatus of CC1, wherein said inspection apparatus has a button which when depressed initiates said freeze frame mode control signal, wherein said inspection apparatus is configured so that said freeze frame mode is deactivated when said button is released.

CC6. The inspection apparatus of CC1, wherein said inspection apparatus is configured to output a specialized illumination on time pulse responsively to said freeze frame mode control signal being initiated.

CC7. The inspection apparatus of CC1, wherein said inspection apparatus is configured to output a specialized illumination on time pulse responsively to said freeze frame mode control signal being initiated, said specialized illumination on time pulse having a higher peak power level than an illumination on time pulse output by said inspection apparatus prior to a time of initiation of said freeze frame mode control signal.

CC8. The inspection apparatus of CC1, wherein said inspection apparatus is configured to output a specialized illumination on time pulse responsively to said freeze frame mode control signal being initiated, said specialized illumination on time pulse having a reduced pulse width relative to an illumination on time pulse output by said inspection apparatus prior to a time of initiation of said freeze frame mode control signal.

CC9. The inspection apparatus of CC1, wherein said inspection apparatus is configured to output a specialized illumination on time pulse responsively to said freeze frame mode control signal being initiated, said specialized illumination on time pulse having a lower peak power level relative to an illumination on time pulse output by said inspection apparatus prior to a time of initiation of said freeze frame mode control signal.

CC10. The inspection apparatus of CC1, wherein said inspection apparatus is configured to output a specialized illumination on time pulse responsively to said freeze frame mode control signal being initiated, said specialized illumination on time pulse being different than an illumination on time pulse output by said inspection apparatus prior to a time of initiation of said freeze frame mode control signal and having a characteristic determined responsively to a processing of image data by said inspection apparatus.

DD1. An inspection apparatus comprising:
an elongated inspection tube;
a head assembly disposed at a distal end of said elongated inspection tube;
a two dimensional image sensor generating image signals;
a base assembly disposed at a proximal end of said elongated inspection tube;
a display disposed on said base assembly;
at least one light source bank for outputting light that is projected outwardly from said head assembly;
wherein said inspection apparatus is configured to output on said display a live streaming video image;
wherein said inspection apparatus is configured so that a strobe mode control signal for activating a strobe mode can be initiated at a time at which said inspection apparatus outputs to said display said live streaming video image;
wherein said inspection apparatus is further configured so that said apparatus, when said strobe mode has been made active processes image data to determine a timing of a moving component represented in the image data and establishes a timing of a light source bank driver signal for driving said at least one light source bank responsively to the processing for determining a timing of a moving component.

DD2. The inspection apparatus of DD1, wherein said inspection apparatus is configured so that said strobe mode control signal can be initiated responsively to an actuation of an actuator by an inspector.

DD3. The inspection apparatus of DD1, wherein said inspection apparatus is configured so that said strobe mode control signal can be initiated responsively to sensing of a condition by said inspection apparatus.

DD4. The inspection apparatus of DD1, wherein said inspection apparatus is configured so that said strobe mode control signal can be initiated responsively to an actuation of an actuator by an inspector or a sensing of a condition by said inspection apparatus.

DD5. The inspection apparatus of DD1, wherein said inspection apparatus, when said strobe mode has been made active processes image data to determine a frequency of a moving component represented in said image data and establishes a frequency of an illumination on pulse forming said light source bank driver signal responsively to said processing for determining a frequency of said moving component.

DD6. The inspection apparatus of DD1, wherein said inspection apparatus, when said strobe mode has been made active processes image data to determine a frequency of a moving component represented in said image data and establishes a frequency of an exposure control signal responsively to said processing for determining a frequency of said moving component.

EE1. An inspection apparatus comprising:
an elongated inspection tube;
a head assembly disposed at a distal end of said elongated inspection tube;
a two dimensional image sensor generating image signals;
a base assembly disposed at a proximal end of said elongated inspection tube;
a display disposed on said base assembly;
at least one light source bank for outputting light that is projected outwardly from said head assembly;
wherein said inspection apparatus is configured to output on said display a live streaming video image;
wherein said inspection apparatus is configured so that an in-motion control signal for activating an in-motion mode can be initiated at a time at which said inspection apparatus outputs to said display said live streaming video image;
wherein said inspection apparatus is further configured so that said apparatus, when said in-motion mode has been made active reduces a width of an illumination on time pulse forming a light source bank driver signal for driving said at least one light source bank responsively to the in-motion mode control signal being made active, the inspection apparatus being configured to maintain said illumination on-time pulse at a reduced pulse width for a period during which said in-motion mode remains active.

EE2. The inspection apparatus of EE1, wherein said inspection apparatus is configured so that said in-motion mode control signal can be initiated responsively to an actuation of an actuator by an inspector.

EE3. The inspection apparatus of EE1, wherein said inspection apparatus is configured so that said in-motion mode control signal can be initiated responsively to sensing of a condition by said inspection apparatus.

EE4. The inspection apparatus of EE1, wherein said inspection apparatus is configured so that said in-motion mode control signal can be initiated responsively to an actuation of an actuator by an inspector or a sensing of a condition by said inspection apparatus.

FF1. An inspection apparatus for inspecting a target, said inspection apparatus comprising:
an elongated inspection tube;
a head assembly disposed at a distal end of said elongated inspection tube, said head assembly having an imaging lens;
an image sensor generating image signals;
at least one light source bank for illuminating said target; and
a user interface enabling an operator of said inspection apparatus to cause activation of a specialized mode of operation;
wherein said apparatus is configured to output a light source bank driver signal for driving said at least one light source bank such that said at least one light source bank has illumination on periods and illumination off periods, the illumination off periods being intermediate the illumination on periods,
wherein said apparatus is further configured so that when said specialized operating mode is made active, said illumination on periods become shorter and said illumination off periods become longer.

FF2. The inspection apparatus of FF1 wherein said user interface includes a button which when actuated results in said specialized operating mode being made active.

FF3. The inspection apparatus of FF1, wherein said apparatus is configured to detect motion, and where said inspection apparatus is further configured so that said specialized operating mode can be made active responsively to an in-motion condition being sensed.

FF3. The inspection apparatus of FF1, wherein said apparatus is configured to detect motion, and where said inspection apparatus is further configured so that said specialized operating mode can be made active responsively to a processing of image data.

While apparatuses, methods and systems described herein as having a certain number of elements, it will be understood that the described apparatuses, methods, and systems can be provided in forms having fewer than the described number of elements. The term "adapted" herein has the same meaning as the term "configured."

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An inspection apparatus for inspecting a target, said inspection apparatus comprising:
an elongated inspection tube having a proximal end and a distal end, the elongated inspection tube comprising:
a head assembly disposed at the distal end of said elongated inspection tube, said head assembly having an imaging lens;
a base assembly coupled to the inspection tube at the proximal end of the inspection tube, said base assembly comprising:
an image sensor generating image signals representing said target; and
a light source bank comprising at least one LED; and
a fiber optic bundle disposed in said elongated inspection tube for receiving image forming light rays of the target from the imaging lens and relaying the image forming light rays of the target to the image sensor in the base assembly, the fiber optic bundle being arranged to conduct light from said light source bank in the base assembly to, and outwardly from, said head assembly.

2. The inspection apparatus of claim 1, wherein said light source bank comprises a plurality of LEDs.

3. An inspection apparatus comprising:
an elongated inspection tube having a proximal end and a distal end, the elongated inspection tube comprising:
a camera head assembly disposed at the distal end of said elongated inspection tube, said camera head assembly having an imaging lens and an image sensor generating image signals;
a base assembly coupled to the inspection tube at the proximal end of the inspection tube, said base assembly comprising:
a first light source bank comprising at least one LED;
a fiber optic bundle disposed in said elongated inspection tube and in said base assembly, the fiber optic bundle being arranged to conduct light from said first light source bank in the base assembly and outwardly from said camera head assembly; and
a second light source bank disposed in said head assembly, the second light source bank arranged to conduct light outwardly from said camera head assembly in addition to the light from said first light source bank.

4. The inspection apparatus of claim 3, wherein said inspection apparatus is configured to selectively energize said first light source bank without energizing said second light source bank until a brightness of a captured image falls below a threshold and, and wherein said apparatus is configured to energize both said first light source bank and said second light source bank on the condition that said brightness falls below said threshold.

5. The inspection apparatus of claim 3, wherein said inspection apparatus is configured to sense a temperature of said apparatus and to output a light source bank driver signal responsively to said sensed temperature.

6. The inspection apparatus of claim 3, wherein said inspection apparatus is configured to sense a temperature of said apparatus and to output a light source bank driver signal responsively to said sensed temperature, and wherein for sensing said temperature said apparatus senses a voltage across at least one of said first light source bank or said second light source bank.

7. The inspection apparatus of claim 3, wherein said second light source bank comprises at least one LED.

8. The inspection apparatus of claim 3, wherein said second light source bank comprises at least one laser diode assembly.

9. An inspection apparatus comprising:
an elongated inspection tube;
a head assembly disposed at a distal end of said elongated inspection tube, said head assembly having an imaging lens, the imaging lens for receiving and focusing light rays from a target;
an image sensor for receiving the focused light rays from the imaging lens and for generating image signals representing the target in response to receiving the focused light rays from the imaging lens;
a light source bank coupled to the head assembly for emitting light outwardly from said head assembly toward the target, wherein said light source bank comprises at least one LED;
wherein said apparatus is configured to send alternating exposure control timing signals to said image sensor in such manner that said image sensor alternates sequentially between exposure on periods for receiving the focused light rays from the imaging lens and exposure off periods for not receiving the focused light rays from the imaging lens; and
wherein said apparatus is further configured to output alternating light source bank driver signals for energizing and de-energizing said at least one light source bank, and wherein said light source bank driver signals are coordinated with said exposure control timing signals such that said light source bank alternates sequentially between being energized during said exposure on periods of said image sensor and being de-energized during the exposure off periods of said image sensor.

10. The inspection apparatus of claim 9, wherein said light source bank is disposed in said head assembly.

11. The inspection apparatus of claim 9, wherein said inspection apparatus includes a base assembly disposed at the proximal end of said elongated inspection tube, and wherein said light source bank is disposed in said base assembly.

12. The inspection apparatus of claim 9, wherein said inspection apparatus is configured so that said light source bank driver signal drives said light source bank at less than a maximum duty cycle during said exposure periods.

13. An inspection apparatus comprising:
an elongated inspection tube;
a head assembly disposed at a distal end of said elongated inspection tube, said head assembly having an imaging lens, the imaging lens for receiving and focusing light rays from a target;
an image sensor for receiving the focused light rays from the imaging lens and for generating image signals representing an image of the target in response to receiving the focused light rays from the imaging lens;
at least one light source bank coupled to the head assembly for emitting light outwardly from said head assembly toward the target;
wherein said inspection apparatus is configured to output a light source bank driver signal for controlling an intensity of the light emitted by said at least one light source bank;
wherein said inspection apparatus comprises a processor configured to examine frames of the image signals and to determine an increasing or decreasing brightness of the image of the target represented by said image signals; and wherein said inspection apparatus comprises a regulator coupled to the processor, the regulator for adjusting a power level of said light source bank driver signal for decreasing or increasing the intensity of the light emitted by said at least one light source bank in response to the determination of increasing or decreasing brightness of the image of the target, respectively.

14. The inspection apparatus of claim 13, wherein said inspection apparatus in adjusting the power level of said light source bank driver signal adjusts a peak power level of said light source bank driver signal.

15. The inspection apparatus of claim 13, wherein said inspection apparatus in adjusting the power level of said light source bank driver signal adjusts a duty cycle of said light source bank driver signal.

16. The inspection apparatus of claim 13, wherein said at least one light source bank comprises a single LED.

17. The inspection apparatus of claim 13, wherein said at least one light source bank comprises a plurality of LEDs.

18. The inspection apparatus of claim 13, wherein said at least one light source bank includes a first light source bank disposed at a location spaced apart from said head assembly and a second light source bank disposed in said head assembly.

19. The inspection apparatus of claim 13, wherein said at least one light source bank includes a first light source bank disposed at a location spaced apart from said head assembly and a second light source bank disposed in said head assembly, wherein said inspection apparatus is configured to energize said second light source bank conditionally on the condition that said brightness falls below a threshold brightness.

20. An inspection apparatus comprising:
an elongated inspection tube;
a head assembly disposed at a distal end of said elongated inspection tube, said head assembly having an imaging lens, the imaging lens for receiving and focusing light rays from a target;
an image sensor for receiving the focused light rays from the imaging lens and for generating image signals representing the target in response to receiving the focused light rays from the imaging lens;
at least one light source bank coupled to the head assembly for emitting light outwardly from said head assembly toward the target;
wherein said inspection apparatus is adapted to output a light source bank driver signal for controlling an intensity of the light emitted by said at least one light source bank;
wherein said inspection apparatus comprises a temperature sensor adapted to output a temperature of said image sensor; and
wherein said inspection apparatus comprises a processor coupled to the temperature sensor and configured to receive the temperature of said image sensor and to reduce a power level of said light source bank driver signal for driving said at least one light source bank responsively to said received temperature of said image sensor exceeding a preselected temperature level.

21. The inspection apparatus of claim 20, wherein said temperature sensor includes a thermistor disposed proximate said image sensor, and wherein said inspection apparatus is configured so that in outputting the temperature of said image sensor, said inspection apparatus reads an output of said thermistor.

22. The inspection apparatus of claim 20, wherein said inspection apparatus in outputting a temperature of said image sensor processes said image signals.

23. The inspection apparatus of claim 20, wherein said at least one light source bank is disposed proximate said image sensor, and wherein said inspection apparatus in outputting said temperature senses a voltage across said light source bank.

* * * * *

UNITED STATES PATENT AND TRADEMARK OFFICE
CERTIFICATE OF CORRECTION

PATENT NO. : 8,514,278 B2
APPLICATION NO. : 11/648189
DATED : August 20, 2013
INVENTOR(S) : Karpen et al.

Page 1 of 1

It is certified that error appears in the above-identified patent and that said Letters Patent is hereby corrected as shown below:

In the Specification

In Column 9, Line 58, delete "de-serialized" and insert --de-serializer --, therefor.

In Column 20, Line 23, delete "apparatus of 1," and insert -- apparatus of B1, --, therefor.

Signed and Sealed this
Twelfth Day of November, 2013

Teresa Stanek Rea
*Deputy Director of the United States Patent and Trademark Office*